(12) United States Patent
Kalgutkar et al.

(10) Patent No.: US 6,306,890 B1
(45) Date of Patent: Oct. 23, 2001

(54) ESTERS DERIVED FROM INDOLEALKANOLS AND NOVEL AMIDES DERIVED FROM INDOLEALKYLAMIDES THAT ARE SELECTIVE COX-2 INHIBITORS

(75) Inventors: Amit S. Kalgutkar; Lawrence J. Marnett, both of Nashville, TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/385,748

(22) Filed: Aug. 30, 1999

(51) Int. Cl.[7] .................. A61K 31/4045; A61K 31/405; A61P 29/00; C07D 209/04; C07D 209/18
(52) U.S. Cl. ................. 514/419; 514/235.2; 514/252.06; 514/339; 514/363; 514/365; 514/374; 514/378; 514/406; 514/415; 514/422; 544/143; 544/238; 546/279.1; 548/136; 548/201; 548/236; 548/248; 548/374.1; 548/491; 548/494; 548/495
(58) Field of Search ...................................... 514/415, 419; 548/491, 494, 495

(56) References Cited

U.S. PATENT DOCUMENTS

| | | |
|---|---|---|
| 3,285,908 | 11/1966 | Shen . |
| 3,336,194 | 8/1967 | Shen . |
| 4,229,447 | 10/1980 | Porter . |
| 4,412,994 | 11/1983 | Sloan et al. . |
| 4,851,426 | 7/1989 | Ladkani et al. . |
| 5,016,652 | 5/1991 | Rose et al. . |
| 5,032,588 | 7/1991 | Brooks et al. . |
| 5,436,265 | 7/1995 | Black et al. . |
| 5,504,086 | 4/1996 | Ellinwood, Jr. et al. . |
| 5,510,368 | 4/1996 | Lau et al. . |
| 5,607,966 | 3/1997 | Hellberg et al. . |
| 5,681,964 | 10/1997 | Ashton et al. . |
| 5,811,438 | 9/1998 | Hellberg et al. . |
| 6,048,850 | 4/2000 | Young et al. . |

FOREIGN PATENT DOCUMENTS

| | | |
|---|---|---|
| 190749 | 12/1981 | (CS) . |
| 2735537 | 2/1979 | (DE) . |
| 2926472 | 1/1981 | (DE) . |

(List continued on next page.)

OTHER PUBLICATIONS

Allison et al., "Gastrointestinal Damage Associated with the Use of Nonsteroidal Antiinflammatory Drugs," The New England Journal of Medicine, vol. 327 (No. 11), p. 749–754, (Sep. 10, 1992).

Archibald et al., "Synthesis and Hypotensive Activity of Benzamido–piperidylethylindoles," Journal of Medicinal Chemistry, vol. 14(No. 11), p. 1054–1059, (Mar. 12, 1971).

Black et al., "From Indomethacin to a Selective COX–2 Inhibitor: Development of Indolalkanoic Acids as Potent and Selective Cyclooxygenase–2 Inhibitors," Bioorganic & Medicinal Chemistry Letters vol. 6 (No. 6), p. 725–730, (1996).

(List continued on next page.)

*Primary Examiner*—Jane C. Oswecki
(74) *Attorney, Agent, or Firm*—Jenkins & Wilson, P.A.

(57) ABSTRACT

A compound of the formula

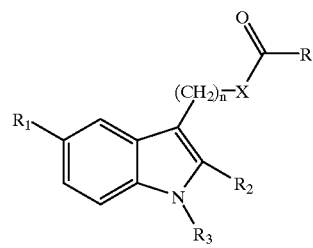

where:

n, and

X are as defined in the specification, and the compound possesses selectivity for inhibition of cyclooxygenase-2.

10 Claims, 3 Drawing Sheets

Inhibition of COX-2 in Activated RAW264.7 Macrophages

FOREIGN PATENT DOCUMENTS

| | | |
|---|---|---|
| 3145465 | 5/1983 | (DE) . |
| 3235850 | 8/1983 | (DE) . |
| 3206885 | 9/1993 | (DE) . |
| 51278 A1 | 5/1982 | (EP) . |
| 144845 A1 | 6/1985 | (EP) . |
| 327766 A2 | 8/1989 | (EP) . |
| 335164 A2 | 10/1989 | (EP) . |
| 335545 A2 | 10/1989 | (EP) . |
| 342682 A2 | 11/1989 | (EP) . |
| 432545 | 11/1976 | (ES) . |
| 2392008 | 12/1978 | (FR) . |
| 54090174 | 7/1979 | (JP) . |
| 58201763 | 11/1983 | (JP) . |
| 59161358 | 9/1984 | (JP) . |
| 61060649 | 3/1986 | (JP) . |
| 63196598 | 8/1988 | (JP) . |
| 63275593 | 11/1988 | (JP) . |
| 8105139 | 6/1982 | (NL) . |
| WO 95/04030 | 2/1995 | (WO) . |
| WO 95/20567 | 8/1995 | (WO) . |

OTHER PUBLICATIONS

Boltze et al., "Chemical Structure and Antiinflammatory activity in the Group of Substituted Indole–3–Acetic Acids," Arzneim–Forsch/Drug Res., vol. 30(II)(No. 8a), p. 1314–1325, (1980).

Chan et al., "Pharmacology of a Selective Cyclooxygenase–2 Inhibitor, L–745,337: A Novel Nonsteroidal Anti–inflammatory Agent with an Ulcerogenic Sparing Effect in Rat and Nonhuman Primate Stomach," The Journal of Pharmacology and Experimental Therapeutics, vol. 274 (No. 3), p. 1531–1537, (1995).

DeVane et al., "Isolation and Structure of a Brain Constituent That Binds to the Cannabinoid Receptor," Science, vol. 258, p. 1946–1949, (Dec. 18. 1992).

DeWitt et al., "Primary Structure of Prostaglandin G/H Synthase from Sheep Vesicular Gland Determined from the Complementary DNA Sequence," Proc. Natl. Acad. Sci. USA, vol. 85, p. 1412–1416, (Mar. 1988).

Downing et al., "Enzyme Inhibition by Acetylenic Compounds," Biochemical and Biophysical Research Communications, vol. 40 (No. 1), p. 218–223, (1970).

Downing et al., "Structural Requirements of Acetylenic Fatty Acids for Inhibition of Soybean Lipoxygenase and Prostaglandin Synthetase," Biochimica et Biophysica Acta, vol. 280, p. 343–347, (1972).

Diago–Meseguer et al., "A New Reagent for Activating Carboxyl Groups; Preparation and Reactions of N,N–Bis [2–oxo–3–oxo–azolidinyl]phosphorodiamidic Chloride," Synthesis, p. 547–551, (Jul., 1980).

Fisnerova et al., "Pharmacologically Interesting Indomethacin Derivatives," Heterocycles, vol. 88, p. 373, (1978).

Fisnerova et al., "Esters of 1–(p–chlorobenzoyl)–5–methoxy–2–methyl–3–indolylacetic acid," Heterocycles, vol. 95, p. 667, (1981).

Futaki et al., "NS–398, A New Anti–inflammatory Agent, Selectively Inhibits Prostaglandin G/H Synthase/Cyclooxygenase (COX–2) Activity In Vitro," Prostaglandins, vol. 47, p. 55–59, (Jan., 1994).

Gans et al., "Anti–Inflammatory and Safety Profile of DuP 697, a Novel Orally Effective Prostaglandin Synthesis Inhibitor," The Journal of Pharmacology and Experimental Therapeutics, vol. 254 (No. 1), p. 180–187, (Mar. 27, 1990).

Graedon et al., "Pills Promise Relief Without Ulcers," The News & Observer, p. 8D, (Sep. 13, 1998).

HLA et al., "Human Cyclooxygenase–2 cDNA," Proc. Natl. Acad. Sci. USA, vol. 89, p. 7384–7388, (Aug., 1992).

Kalgutkar et al., "Aspirin–Like Molecules that Covalently Inactivate Cyclooxygenase–2," Science, vol. 280, p. 1268–1270, (May 22, 1998).

Katori et al., "Induction of Prostaglandin H Synthase–2 in Rat Carrageenin–Induced Pleurisy and Effect of a Selective COX–2 Inhibitor," Advances in Prostaglandin, Thromboxane, and Leukotriene Research, vol. 23, p. 345–347, (1995).

Kennedy, "Cloning and Espression of Rat Prostaglandin Endoperoxide Synthase (Cyclooxyganse)–2 cDNA," Biochemical and Biophysical Research Communications, vol. 197 (No. 2), p. 494–500, (Dec. 15, 1993).

Khanna et al., "1,2–Diarylpyrroles as Potent and Selective Inhibitors of Cyclooxygenase–2," Journal of Medicinal Chemistry, vol. 40 (No. 11), p. 1619–1633, (1997).

Kappe et al., "Non–Steroidal Antiinflammatory Agents. V. Basic Esters of Indomethacin," J. Prakt. Chem., vol. 332 (No. 4), p. 475–478, (1990).

Kolasa et al., "Nonsteroidal Anti–Inflammatory Drugs as Scaffolds for the Desing of 5–Lipoxygenase Inhibitors," J. Med. Chem., vol. 40, p. 819–924, (1997).

Kujubu et al., "TIS10, a Phorbol Ester Tumor Promoter–Inducible mRNA from Swill 3T3 Cells, Enclodes a Novel Prostaglandin Synthase/Cyclooxygenase Homologue," J. Biol. Chem., vol. 266 (No. 20), p. 12866–72 (Jul. 15, 1991).

Lee et al., "Selective Expression of Mitogen–Inducible Cyclooxygenase in Macrophages Stimulated with Lipopolysaccharide," The Journal of Biological Chemistry, vol. 267, p. 25934–25938, (Dec. 25, 1992).

Li et al., "Cyclooxygenase–2 Inhibitors. Synthesis and Pharmacological Activities of 5–Methanesulfonamido–1–Indanone Derivatives," Journal of Medicinal Chemistry, vol. 38, p. 4987–4905, (1995).

Li et al., "1,2–Diarylcyclopentenes as Selective Cyclooxygenase–2 Inhibitors and Orally Active Anti–Inflammatory Agents," J. Med. Chem., vol. 38, p. 4570–4578, (1995).

Li et al., "Novel Terphenyls as Selective Cyclooxygenase–2 Inhibitors and Orally Active Anti–Inflammatory Agents," J. Med. Chem., vol. 39, p. 1846–1856, (1996).

Linari et al., "Sunstituted Anilides of 1–(p–Chlorobenzoyl)–5–methoxy–2–methyl–indole–3–acetic Acid," Arzneim–Forsch. (Drug. Res.), vol. 23 (No. 1), p. 89–91, (1973).

Luong et al., "The Structure of Human Cyclooxygenase–2: Conservation and Flexibility of the NSAID Binding Site," Nature Structural Biology, vol. 3, p. 927–933, (1996).

Marnett et al., "Mechanism of the Stimulation of Prostaglandin H Synthase and Prostaglandin Synthase by the Anti-thrombotic and Antimetastatic Agent, Nafazatrom" Molecular Pharmacology, vol. 26, p. 328–335, (1984).

Masferrer et al., "Selective Inhibition of Inducible Cyclooxygenase 2 In Vivo is Antiinflammatory and Nonulcerogenic," Proc. Natl. Acad. Sci. USA, vol. 91, p. 3228–3232, (Apr. 1994).

Meade et al., "Differential Inhibition of Prostaglandin Endoperoxide Synthase (Cyclooxygenase) Isozymes by Aspirin and Other Non–Steroidal Anti–Inflammatory Drugs," The Journal of Biological Chemistry, vol. 238 (No. 9), p. 6610–6614, (Mar. 25, 1993).

Mulders, "Indole Acid Amides," Heterocyclic Compounds, vol. 62, p. 16198–16199, (1965).

Nakamura et al., "Studies on Antiinflammatory Agents II. Synthesis and Pharmacological Properties of 2'-(Phenylthio)methanesulfonanilides and Related Derivatives," Chem. Pharm. Bull., vol. 41 (No. 5), p. 894–906, (1993).

Odenwaller et al., "Preparation and Proteolytic Cleavage of Apoprostaglandin Endoperoxide Synthase," Methods in Enzymology, vol. 187, p. 479–485, (1990).

Ogiso et al., "Pharmacokinetics of Indomethacin Ester Prodrugs: Gastrointestinal and Hepatic Toxicity and the Hydrolytic Capacity of Various Tissues in Rats," Bio. Pharm. Bull, vol. 19 (No. 9), pp. 1178–1183, (1996).

O'Sullivan et al., "Lipopolysaccharide–Induced Expression of Prostaglandin H Synthase–2 in Alveolar Macrophage is Inhibited by Dexamethasone but not by Aspirin," Biochemical and Biophysical Research Communications, vol. 191 (No. 3), p. 1294–1300, (Mar. 31, 1993).

Penning et al., "Synthesis and Biological Evaluation of the 1,5–Diarylpyrazole Class of Cyclooxygenase–2 Inhibitors: Identification of 4–[5–(methylphenyl)–3–(trifluoromethyl)–1H–pyrazol–1–yl]benzenesulfonamide (SC–58635, Celecoxib)," J. Med. Chem., vol. 40 (No. 9), p. 1347–1365, (1997).

Physician's Desk Reference, 41st Edition, pp. 1304–1310 (1987), Indocin® (Indomethacin, MSD).

Prasit et al., "L–745,337: A Selective Cyclooxygenase–2 Inhibitor," Med. Chem. Res., vol. 5, p. 364–374, (1995).

Ramesha, "Human and Rat Cyclooxygenases are Pharmacologically Distinct," Eicosanoids and Other Bioactive Lipids in Cancer Inflammation and Radiation Injury, Chp. 10, p. 67–71, (1997).

Reitz et al., "Novel 1,2–Diarylcyclopentenes are Selective, Potent and Orally Active Cyclooxygenase Inhibitors," Med. Chem. Res., vol. 5, p. 351–363, (1995).

Riendeau et al., "Biochemical and Pharmacological Profile of Tetrasubstituted Furanone as a Highly Sensitive COX–2 Inhibitor," British J. Pharmacol., vol. 121, p. 105–117, (1997).

Roy et al., "A New Series of Selective COX–2 Inhibitors: 5,6–Diarylthiazolo[3,2–b][1,2,4]Triazoles," Bioorganic & Medicinal Chemistry Letters, vol. 7 (No. 1), p. 57–62, (1997).

Sauvaire et al., "Pharmacological Activity and Toxicity of Apyramide: Comparison with Non–Steroidal Anti–Inflammatory Agents," Drugs. Exp. Clin. Res., vol. 13 (No. 5), p. 247–252, (1987).

Shaw, "The Synthesis of Tryptamines Related to Serotonin,", vol. 77, Journal of the American Chemical Society, p. 4319–4324, (Aug. 20, 1955).

Smith et al., "Prostaglandin Endoperoxide H Synthases (Cyclooxygenases)–1 and 2," The Journal of Biological Chemistry, vol. 271 (No. 52), p. 33157–60, (Dec. 27, 1996).

Soai et al., "Mixed Solvents Containing Methanol as Useful Reaction Media for Unique Chemoselective Reductions with Lithium Borohydride," J. Org. Chem., vol. 51 (No. 21), p. 4000–4005, (1986).

Tammara et al., "Synthesis and Evaluation of Morpholinoalkyl Ester Prodrugs of Indomethacin and Naproxen," Pharmaceutical Research, vol. 10 (No. 8), p. 1191–1199, (1993).

Tanaka et al., "Pharmacological Studies of the New Antiinflammatory Agent 3–Formylamino–7–Methylsulfonylamino–6–Phenoxy–4H–1–Benzopyran–4–One," Arzneim–Forsch/Drug Res., vol. 42(II) (No. 7), p. 935–944, (1992).

Therien et al., "Synthesis and Biological Evaluation of 5,6–Diarylimidazo[2.1–b]Thiazole as Selective COX–2 Inhibitors," Bioorganic & Medicinal Chemistry Letters, vol. 7 (No. 1), p. 47–52, (1997).

Tsuji et al., "Studies on Anti–Inflammatory Agents. IV. Synthesis and Pharmacological Properties of 1,5–Diarylpyrazoles and Related Derivatives," Chem. Pharm. Bull., vol. 45 (No. 6), p. 987–995, (1997).

Vane et al., "Inducible Isoforms of Cyclooxygenase and Nitric–Oxide Synthase in Inflammation," Proc. Natl. Acad. Sci. USA, vol. 91, p. 2046–2050, (Mar., 1994).

Pal et al., "7–Oxabicycloheptylprostanoic Acids: Potent, Time–Dependent Cyclooxygenase Inhibitors That Induce a Conformational Change in the Prostaglandin Endoperoxide Synthase Protein," Journal of Medicinal Chemistry, vol. 35 (No. 12), p. 2340–2342, (1992).

Flynn et al., "Nonsteroidal Antiinflammatory Drug Hydroxamic Acids. Dual Inhibitors of Both Cyclooxygenase and 5–Lipoxygenase," J. Med. Chem., vol. 33 (No. 8), p. 2070–2072, (1990).

Wang et al., "A Selective Method for the Preparation of Primary Amides: Synthesis of Fmoc–L–4–Carboxamidophenylalanine and Other Compounds," Tetrahedron Letters, vol. 40, p. 2501–2504, (Jan., 1999).

Wiesenberg–Boettcher et al., "The Pharmacological Profile of CGP 28238, A Novel Highly Potent Anti–Inflammatory Compound," Drug Exp. Clin. Res., vol. 15 (No. 11–12), p. 501–509, (1989).

Yu et al., "Synthesis of Prostaglandin E2 Ethanolamide from Anandamide by Cyclooxygenase–2," The Journal of Biological Chemistry, vol. 272 (No. 34), p. 21181–86, (Aug. 22, 1997).

Yokoyama et al., "Cloning of Human Gene Encoding Prostaglandin Endoperoxide Synthase and Primary Structure of the Enzyme," Biochemical and Biophysical Research Communications, vol. 165 (No. 2), p. 888–894, (Dec. 15, 1989).

Barasoain et al., "Immunosuppressive Effects of Some Organic Compounds with Anti–Inflammatory Activity," Chemother. Proc. Int. Congr. Chemother., vol. 8, p. 21–26, (1976).

Barasoain et al., "Indomethacin Esters Acting as Anti–Inflammatory and Immunosuppressive Drugs," Int. J. Clin. Pharmacol. Biopharm., vol. 16 (No. 5), p. 235–239, (1978).

Bonina et al., "In Vitro and In Vivo Evaluation of Polyoxyethylene Indomethacin Esters as Dermal Prodrugs," J. Controlled Release, vol. 34 (No. 3 br273), p. 223–232, (1995).

Davarin et al., "Acrylic Type Polymers Containing Ibuprofen and Indomethacin with Difunctional Spacer Group: Synthesis and Hydrolysis," J. Controlled Release, vol. 47 (No. 1), p. 41–49, (1997).

Decaprariis et al., "Synthesis and Pharmacological Evaluation of Oligoethylene Ester Derivatives as Indomethacin Oral Prodrugs," J. Pharm. Sci., vol. 83 (No. 11), p. 1578–1581, (1994).

Fisnerova et al., "Esters of 1–(p–chlorobenzoyl)–5–methoxy–2–methyl–3–indolylacetic Acid," Collect. Czech. Chem. Commun., vol. 45 (No. 3), p. 901–905, (1980).

Kwapiszewski et al., "Synthesis of N–[1–(p–chlorobenzoyl)–5–methoxy–2–methyl–3–indoleacetyl] Amino Acids and Their Esters," Acta. Pol. Pharm., vol. 39 (No. 5–6), p. 327–336, (1982).

Makovec et al., "Pharmacokinetics and Metabolism of [14C]–Proglumetacin after Oral Administration in the Rat," Arzneim.–Forsch, vol. 37 (No. 7), p. 806–813, (1987).

McClean et al., "Synthesis and Pharmacological Evaluation of Conjugates of Prednisolone and Non–Steroidal Anti–Inflammatory Agents," Steroids, vol. 54 (No. 4), p. 421–439, (1989).

Otis et al., "Synthesis and Pharmacological Evaluation of Amide Derivatives of Nonsteroidal Anti–Inflammatory Drugs," Inflammopharmacology, vol. 1 (No. 3), p. 201–212, (1992).

Phelan et al., "Improved Delivery through Biological Membranes. XXXVII. Synthesis and Stability of Novel Redox Derivatives of Naproxen and Indomethacin," Pharm. Res., vol. 6 (No. 8), p. 667–676, (1989).

Rojo et al., "Variable Effects of Indomethacin and Four Related Compounds on Lymphocyte Blastogenesis and Cell–Mediated Cytotoxicity," Int. J. Clin. Pharmacol., Ther. Toxicol., vol. 19 (No. 9), p. 420–424, (1981).

Rojo et al., "Variation in the Immunosuppressive Activity by Structural Modifications of a Series of Non–Steroidal Anti-inflammatory Drugs (Indomethacin Esters)," Arch. Farmacol. Toxicol., vol. 4 (No. 3), p. 287–292, (1978).

Svoboda et al., "Potential Anti–Inflammatory Agents Based on Indomethacin Esters," Cesk. Farm., vol. 40 (No. 2), p. 71–74, (1991).

Yamawaki et al., "Piperazinealkanol Ester Derivatives of Indomethacin as Dual Inhibitors of 5–lipoxygenase and Cyclooxygenase," Chem. Pharm. Bull., vol. 42 (No. 4), p. 963–971, (1994).

ESTERS DERIVED FROM INDOLEALKANOLS AND NOVEL AMIDES DERIVED FROM INDOLEALKYLAMIDES THAT ARE SELECTIVE COX-2 INHIBITORS

TECHNICAL FIELD

The present invention, in general, relates to ester derivatives and amide derivatives of various indoles, more specifically, esters and amides derived from N-(4-substituted aroyl)- or N-(4-substituted aryl)-5-alkoxy-2-alkylindole-3-alkanols and N-(4-substituted aroyl)- or N-(4-substituted aryl)-5-alkoxy-2-alkylindole-3-alkyl amines, which resultant esters and amides exhibit inhibition of cyclooxygenase-2 (COX-2) far exceeding inhibition of cyclooxygenase-1 (COX-1), and also, which still exhibit an analgesic, antiinflammatory, and/or antipyretic effect like that of the indole known as indomethacin (an NSAID), in warm blooded vertebrate animals, including humans.

Table of Abbreviations

| Abbreviations | Definitions |
|---|---|
| AcOH | acetic acid |
| CH$_2$Ph | benzyl |
| C(O)Ph | benzoyl |
| BOP-Cl | bis(2-oxo-3-oxazolidinyl)phosphonic chloride (sold by Aldrich in Wisconsin), and also see the journal article, Diago-Meseguer, Palomo-Coll, Fernandez-Lizarbe, and Zugaza-Bilbao, "New Reagent for Activating Carboxyl Groups; Preparation and Reactions of N,N-Bis[2-oxo-3-oxazolidinyl] phosphorodiamidic Chloride", Synthesis (1980) pp. 547–551 |
| COOH | carboxylic acid moiety |
| CID | collision-induced dissociation |
| IC$_{50}$ | concentration in $\mu$M of indomethacin (or indomethacin derivative) at which there is 50% inhibition of COX activity--the lower IC$_{50}$ is, then the more potent the drug is |
| COX | cyclooxygenase |
| CDCl$_3$ | deuteriated chloroform |
| DCC | dicyclohexylcarbodiimide |
| Et$_2$O | diethyl ether |
| DIPEA | diisopropylethyl amine |
| DMF | dimethyl formamide |
| DMSO | dimethyl sulfoxide |
| DMEM | Dulbecco's modified essential medium |
| ESI | electrospray ionization |
| EtOAc | ethyl acetate |
| FBS | fetal bovine serum |
| 4-BBBr | 4-bromobenzyl bromide |
| 4-CBC | 4-chlorobenzoyl chloride |
| DMAP | 4-dimethylamino pyridine |
| GI | gastrointestinal |
| HPLC | high performance liquid chromatography |
| HOBt | hydroxybenzotriazole |
| IFN-g | interferon gamma |
| kg | kilogram |
| LPS | lipopolysaccharide |
| LiBH$_4$ | lithium borohydride |
| mp | melting point |
| MeOH | methyl alcohol |
| $\mu$L | microliter |
| $\mu$M | micromole/liter |
| mg | milligram |
| mL | milliliter |
| NSAID | non-steroidal antiinflammatory drug |
| N | normal (when used in conjunction with acid concentrations) |
| NMR | nuclear magnetic resonance |
| $^{14}$C-AA | [1-$^4$C]-arachidonic acid |
| EDCl | 1-(3-dimethylaminopropyl)-3-ethyl carbodiimide.HCl |
| (COOH)$_2$ | oxalic acid |
| PER | peroxidase |
| Ph | phenyl |
| PBS | phosphate-buffered saline |
| PGD$_2$ | prostaglandin D$_2$ |
| PGE$_2$ | prostaglandin E$_2$ |
| PGHS | prostaglandin endoperoxide synthase |
| PGH$_2$ | prostaglandin H$_2$ |
| rt | room temperature (about 72° F., 22° C.) |
| SDS PAGE | sodium dodecyl sulfate poly-acrylamide gel electrophoresis |
| NaH | sodium hydride |
| SF-9 | spodoptera frugiperda |
| SAR | structure-activity relationship |
| BOC | tert-butoxy carbonyl |
| THF | tetrahydrofuran |
| TLC | thin layer chromatography |
| Et$_3$N | triethyl amine |

BACKGROUND OF THE INVENTION

As discussed in more detail below, the COX enzyme is really two enzymes, COX-1 and COX-2, which serve different physiological and pathophysiological functions. See, DeWitt and Smith, "Primary Structure of Prostaglandin G/H Synthase from Sheep Vesicular Gland Determined from the Complementary DNA Sequence", *Proc. Natl. Acad. Sci. U.S.A.* (1988) Vol. 85, pp. 1412–1416. As is well known, at antiinflammatory and/or analgesic doses, indomethacin, aspirin, and other NSAIDs effect great inhibition of COX-1, which protects the lining of the stomach from acid, along with relatively minimal inhibition of COX-2, which provokes inflammation in response to joint injury or a disease like arthritis. Also, certain NSAIDs exhibit essentially the same inhibitory activity against both COX-1 and COX-2. The fact that all of the currently marketed NSAIDs inhibit both isozymes to different extents is thought to account for their antiinflammatory activity as well as their GI liabilities. Thus, targeting the inhibition of COX-2 alone has been the goal of drug developers for several years in order to reduce or to eliminate the GI irritation caused by COX-1 inhibition.

More specifically, prostaglandins (particularly prostaglandin E$_2$) are important mediators of inflammation and are also involved in a cytoprotective role in the gastric mucosa. These bioactive molecules are biosynthesized by conversion of arachidonic acid to prostaglandin H$_2$, which is catalyzed by prostaglandin endoperoxide synthase (PGHS or COX). See, Marnett and Kalgutkar, "Design of Selective Inhibitors of Cyclooxygenase-2 as Nonulcerogenic Antiinflammatory Agents", Vol. 2, *Curr. Op. Chem. Biol.*, pp. 482–490 (1998).

As discussed in Smith, Garavito, and DeWitt, "D.L. Prostaglandin Endoperoxide H Synthases (Cyclooxygenases) -1 and -2", *J. Biol. Chem.*, (1996) Vol. 271, pp. 33157–33160, the pertinent step in prostaglandin and thromboxane biosynthesis involves the conversion of arachidonic acid to PGH$_2$, which is catalyzed by the sequential action of the COX and PER activities of PGHS, as set out in the following reaction scheme:

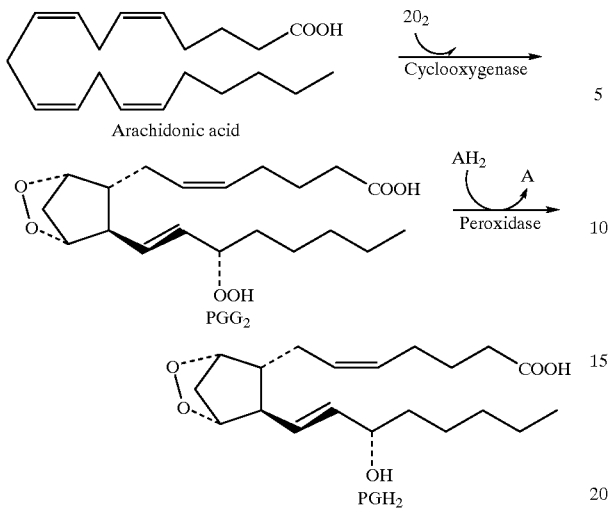

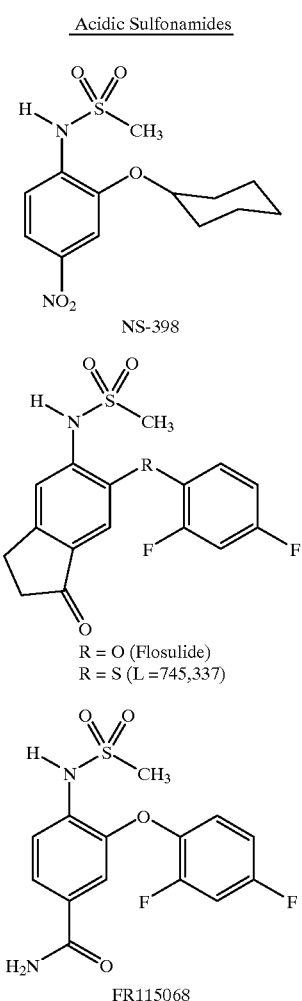

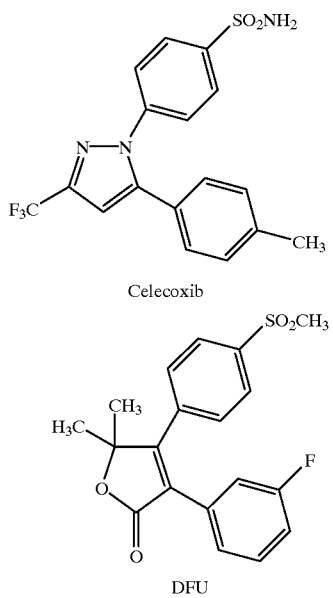

COX-1 is the constitutive isoform and is mainly responsible for the synthesis of cytoprotective prostaglandins in the GI tract and for the synthesis of thromboxane, which triggers platelet aggregation in blood platelets. On the other hand, COX-2 is inducible and short-lived. Its expression is stimulated in response to endotoxins, cytokines, and mitogens. Importantly, COX-2 plays a major role in prostaglandin biosynthesis in inflammatory cells (monocytes/macrophages) and in the central nervous system.

Hence, the difference in the function of COX-1 and COX-2 provides a goal of separating toxicity from efficacy of NSAIDs by developing drugs that are selective COX-2 inhibitors (i.e., specificity for inhibition of COX-2 far exceeds inhibition of COX-1) as antiinflammatory, analgesic, and/or antipyretic agents with minimization of or without the GI and hematologic liabilities from COX-1 inhibition that plague most all currently marketed NSAIDs, most of which inhibit both COX-1 and COX-2, with specificity for COX-1 inhibition greatly exceeding that for COX-2 inhibition, although some have essentially similar inhibitory activity against both COX-1 and COX-2. See, for instance, Meade, Smith, and DeWitt, "Differential Inhibition of Prostaglandin Indoperoxide Synthase (Cyclooxygenase) Isozymes by Aspirin and Other Non-Steroidal Antiinflammatory Drugs", *J. Biol. Chem.*, (1993) Vol. 268, pp. 6610–6614.

Detailed SAR studies have been reported for two general structural classes (certain acidic sulfonamides and certain diarylheterocyclics) of selective COX-2 inhibitors (specificity for COX-2 inhibition far exceeds COX-1 inhibition). The in vivo activities of these selective COX-2 inhibitors validate the concept that selective COX-2 inhibition is antiinflammatory and nonulcerogenic. Specifically, in vivo efficacy studies with the diarylheterocycle class of selective COX-2 inhibitors have not only validated the hypothesis, but have also resulted in the approval of the first selective COX-2 inhibitor, namely celecoxib (sold under the trade name CELEBREX by Monsanto/Searle) for marketing in the United States.

-continued

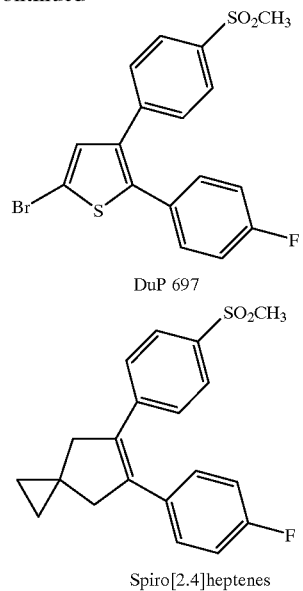

DuP 697

Spiro[2.4]heptenes

Although acidic sulfonamides and diarylheterocyclics have been extensively studied as selective COX-2 inhibitors, there are very few reports on converting NSAIDs that are selective COX-1 inhibitors into selective COX-2 inhibitors. However, U.S. Pat. No. 5,681,964 (issued in 1997) to Ashton et al., assignors to the University of Kentucky Research Foundation, shows conversion of indomethacin (an NSAID) into certain ester derivatives with concomitant reduction of GI irritation (see, FIG. 1 of U.S. Pat. No. 5,681,964 for the structure of the ester derivatives); and U.S. Pat. Nos. 5,607,966 (Parent) (issued in 1997) and 5,811,438 (CIP) (issued in 1998), both to Hellberg et al., assignors to Alcon Laboratories, show conversion of various NSAIDs (such as indomethacin) into certain ester derivatives and amide derivatives (that are useful as antioxidants and inhibitors of 5-lipoxygenase), but do not address selective COX-2 inhibition. Moreover, U.S. Pat. Nos. 5,436,265 (issued in 1995) to Black et al. and 5,510,368 (issued in 1996) to Lau et al., both patents assigned to Merck Frosst Canada, Inc., describe, respectively, 1-aroyl-3-indolyl alkanoic acids and N-benzyl-3-indoleacetic acids as COX-2 selective inhibitors.

In the present investigation, the possibility has been explored for designing selective COX-2 inhibitors using as templates various indoles.

However, nothing in the above-discussed literature suggests that converting certain indole ethanols into esters or certain indole ethylamines into amides would result in compounds that are selective for COX-2 inhibition. Thus, it would be desirable to find certain drugs which are selective COX-2 inhibitors (display an inhibition for COX-2 far exceeding inhibition for COX-1), as well as possess an analgesic, antiinflammatory, and/or antipyretic effect like that possessed by the drug, indomethacin, or by other well known NSAIDs.

SUMMARY AND OBJECTS OF THE INVENTION

Surprisingly with the present invention, it has been found that derivatization of the ethanol moiety or the ethylamine moiety of various indoles to precursor ester analogs or to precursor amide analogs, followed by N-acylation or N-alkylation of the indole nitrogen, creates isozyme specificity for COX-2. Moreover, the resultant inventive N-acylated or N-alkylated ester or inventive N-acylated or N-alkylated amide is not only a selective COX-2 inhibitor, but also possesses an analgesic, antiinflammatory, and/or antipyretic effect.

Therefore, the present invention provides a compound of the formula

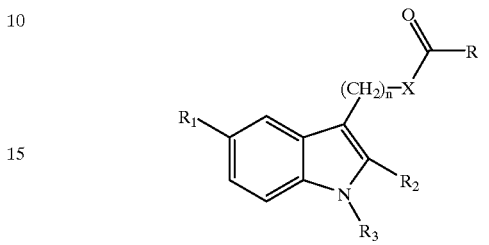

where:
R=$C_1$ to $C_6$ alkyl, $C_1$ to $C_6$ branched alkyl, $C_4$ to $C_8$ cycloalkyl, $C_1$ to $C_6$ hydroxyalkyl, branched $C_1$ to $C_6$ hydroxyalkyl, hydroxy substituted $C_4$ to $C_8$ aryl, primary, secondary or tertiary $C_1$ to $C_6$ alkylamino, primary, secondary or tertiary branched $C_1$ to $C_6$ alkylamino, primary, secondary or tertiary $C_4$ to $C_8$ arylamino, $C_1$ to C6 alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ aryl, $C_4$ to $C_8$ arylcarboxylic acid, $C_4$ to $C_8$ arylester, $C_4$ to $C_8$ aryl substituted $C_1$ to $C_6$ alkyl, $C_4$ to $C_8$ heterocyclic alkyl or aryl with O, N or S in the ring, alkyl-substituted or aryl-substituted $C_4$ to $C_8$ heterocyclic alkyl or aryl with O, N or S in the ring, or halo-substituted versions thereof, where halo is chloro, bromo, fluoro or iodo, $R_1$=$C_1$ to $C_6$ alkyl, $C_1$ to $C_6$ branched alkyl, $C_4$ to $C_8$ cycloalkyl, $C_4$ to $C_8$ aryl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, or halo-substituted versions thereof or $R_1$ is halo where halo is chloro, fluoro, bromo, or iodo, $R_2$=hydrogen, $C_1$ to $C_6$ alkyl or $C_1$ to $C_6$ branched alkyl, $R_3$=$C_1$ to $C_6$ alkyl, $C_4$ to $C_8$ aroyl, $C_4$ to $C_8$ aryl, $C_4$ to $C_8$ heterocyclic alkyl or aryl with O, N or S in the ring, $C_4$ to $C_8$ aryl-substituted $C_1$ to $C_6$ alkyl, alkyl-substituted or aryl-substituted $C_4$ to $C_8$ heterocyclic alkyl or aryl with O, N or S in the ring, alkyl-substituted $C_4$ to $C_8$ aroyl, or alkyl-substituted $C_4$ to $C_8$ aryl, or halo-substituted versions thereof where halo is chloro, bromo, or iodo, n=1, 2, 3, or 4, and X=O, NH, or N—$R_4$, where $R_4$=$C_1$ to $C_6$ alkyl or $C_1$ to $C_6$ branched alkyl, and the compound possesses selectivity for inhibition of cyclooxygenase-2.

Hence, it is an object of the invention to provide a drug that minimizes or obviates GI irritation. Moreover, it is an advantage of the present invention that the drug is also analgesic, antiinflammatory, and/or antipyretic.

Some of the objects of the invention having been stated above, other objects will become evident as the description proceeds, when taken in connection with the Laboratory Examples and Figure as described below.

DETAILED DESCRIPTION OF THE INVENTION

Figure 1:
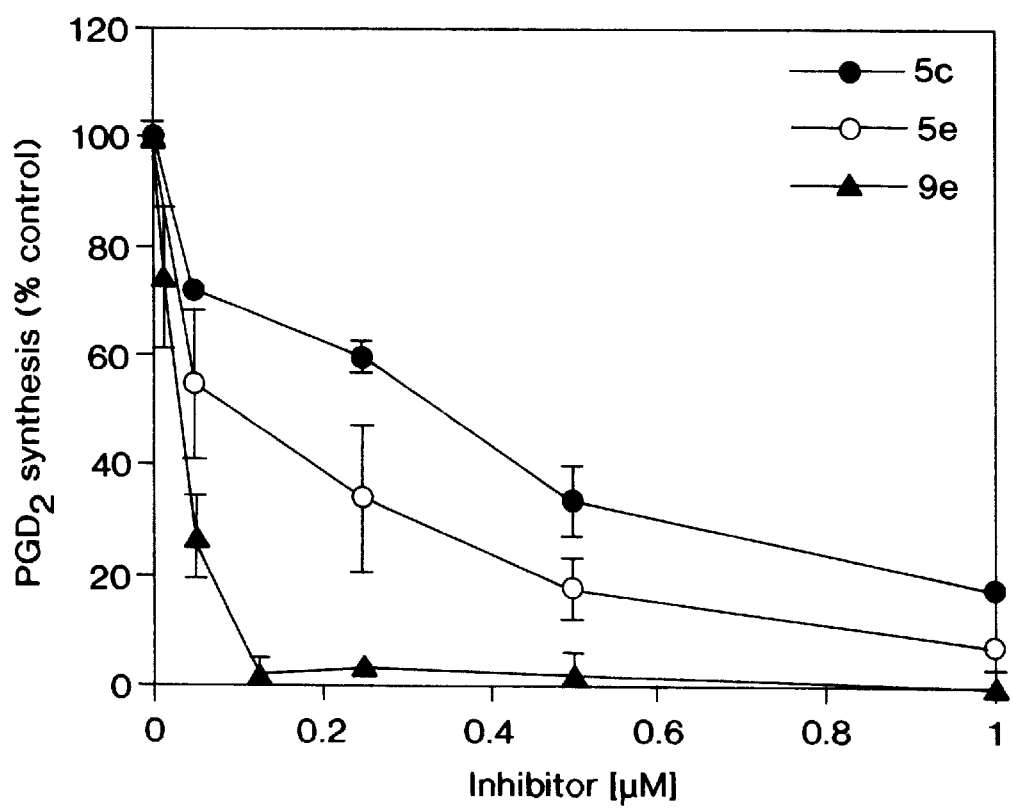
FIG. 1 is a graph illustrating the inhibition of production of $PGD_2$ in cultured inflammatory RAW264.7 cells by Compounds 5c, 5e, and 9e.

The present invention involves a method for converting certain indoles into COX-2 selective inhibitors and also for using the COX-2 selective inhibitors for treating an animal that is a warm-blooded vertebrate. Therefore, the invention concerns mammals and birds.

The preferred inventive compounds useful in the present invention are esters and amides of the following Formulae I and II,

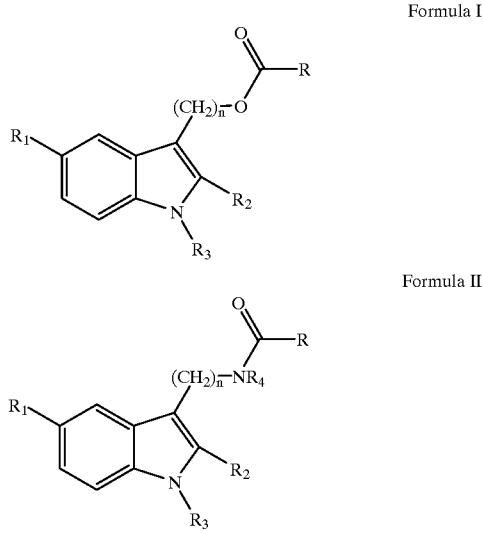

Formula I

Formula II where:
R=$C_1$ to $C_6$ alkyl, $C_1$ to $C_6$ branched alkyl, $C_4$ to $C_8$ cycloalkyl, $C_1$ to $C_6$ hydroxyalkyl, branched $C_1$ to $C_6$ hydroxyalkyl, hydroxy substituted $C_4$ to $C_8$ aryl, primary, secondary or tertiary $C_1$ to $C_6$ alkylamino, primary, secondary or tertiary branched $C_1$ to $C_6$ alkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ aryl, $C_4$ to $C_8$ arylcarboxylic acid, $C_4$ to $C_8$ arylester, $C_4$ to $C_8$ aryl substituted $C_1$ to $C_6$ alkyl, $C_4$ to $C_8$ heterocyclic alkyl or aryl with O, N or S in the ring, alkyl-substituted or aryl-substituted $C_4$ to $C_8$ heterocyclic alkyl or aryl with O, N or S in the ring, or halo-substituted versions thereof, where halo is chloro, bromo, fluoro or iodo, $R_1$=$C_1$ to $C_6$ alkyl, $C_1$ to $C_6$ branched alkyl, $C_4$ to $C_8$ cycloalkyl, $C_4$ to $C_8$ aryl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, or halo-substituted versions thereof or $R_1$ is halo where halo is chloro, fluoro, bromo, or iodo, $R_2$=hydrogen, $C_1$ to $C_6$ alkyl or $C_1$ to $C_6$ branched alkyl, $R_3$=$C_1$ to $C_6$ alkyl, $C_4$ to $C_8$ aroyl, $C_4$ to $C_8$ aryl, $C_4$ to $C_8$ heterocyclic alkyl or aryl with O, N or S in the ring, $C_4$ to $C_8$ aryl-substituted $C_1$ to $C_6$ alkyl, alkyl-substituted or aryl-substituted $C_4$ to $C_8$ heterocyclic alkyl or aryl with O, N or S in the ring, alkyl-substituted $C_4$ to $C_8$ aroyl, or alkyl-substituted $C_4$ to $C_8$ aryl, or halo-substituted versions thereof where halo is chloro, bromo, or iodo, n=1, 2, 3, or 4, and $R_4$=hydrogen, $C_1$ to $C_6$ alkyl or $C_1$ to $C_6$ branched alkyl, and the compound possesses selectivity for inhibition of cyclooxygenase-2.

Compounds of Formulae 1 and 2 possess selectivity for inhibition of cyclooxygenase-2.

More specifically, preferred esters and amides useful in the present invention include, but are not limited to, derivatives of, respectively, esterified 5-methoxy-2-methylindole-3-ethanol and amidated 5-methoxy-2-methylindole-3-ethylamine, where the indole nitrogen has been N-acylated or N-alkylated. Even more preferred are the esters including, but not limited to, N-(p-chlorobenzoyl)-5-methoxy-2-methylindole-3-ethyl-valerate, N-(p-chlorobenzoyl)-5-methoxy-2-methylindole-3-ethyl-(p-methyl)benzoate, N-(p-chlorobenzoyl)-5-methoxy-2-methylindole-3-ethyl-(p-methoxy)benzoate, N-(p-chlorobenzoyl)-5-methoxy-2-methylindole-3-ethyl-(o-methoxy)benzoate, N-(p-chlorobenzoyl)-5-methoxy-2-methylindole-3-ethyl-(p-chloro)benzoate, N-(p-chlorobenzoyl)-5-methoxy-2-methylindole-3-ethyl-(p-bromo)benzoate, N-(p-chlorobenzoyl)-5-methoxy-2-methylindole-3-ethyl-(p-iodo)benzoate, N-(p-bromobenzyl)-5-methoxy-2-methylindole-3-ethyl-(p-chloro)benzoate, and N-(p-chlorobenzoyl)-5-methoxy-2-methylindole-3-ethyl-(2-phenyl)acetate; the amides including but not limited to N-(p-chlorobenzoyl)-5-methoxy-2-methylindole-3-ethyl-valeramide, N-(p-chlorobenzoyl)-5-methoxy-2-methylindole-3-ethyl-(p-methyl)benzamide, N-(p-chlorobenzoyl)-5-methoxy-2-methylindole-3-ethyl-(p-methoxy)benzamide, N-(p-chlorobenzoyl)-5-methoxy-2-methylindole-3-ethyl-(p-chloro)benzamide, N-(p-chlorobenzoyl)-5-methoxy-2-methylindole-3-ethyl-(p-bromo)benamide, N-(p-chlorobenzoyl)-5-methoxy-2-methylindole-3-ethyl-(p-iodo)benzamide, N-(p-bromobenzyl)-5-methoxy-2-methylindole-3-ethyl-(p-chloro)benzamide, and N-(p-chlorobenzoyl)-5-methoxy-2-methylindole-3-ethyl-(2-phenyl)ethylamide; and any combinations of these esters and/or amides.

The general reaction scheme for ester preparation of Compounds 5a through 5h (which scheme may also be employed for ester preparation of Compound 5i) was as follows:

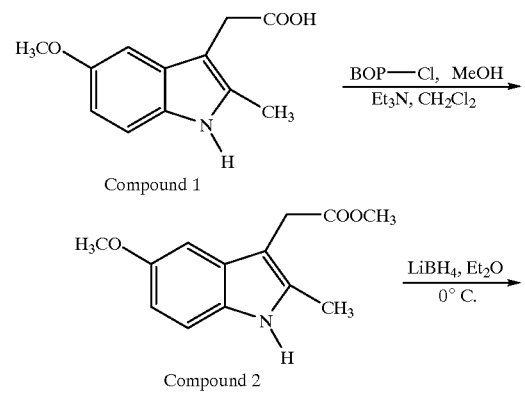

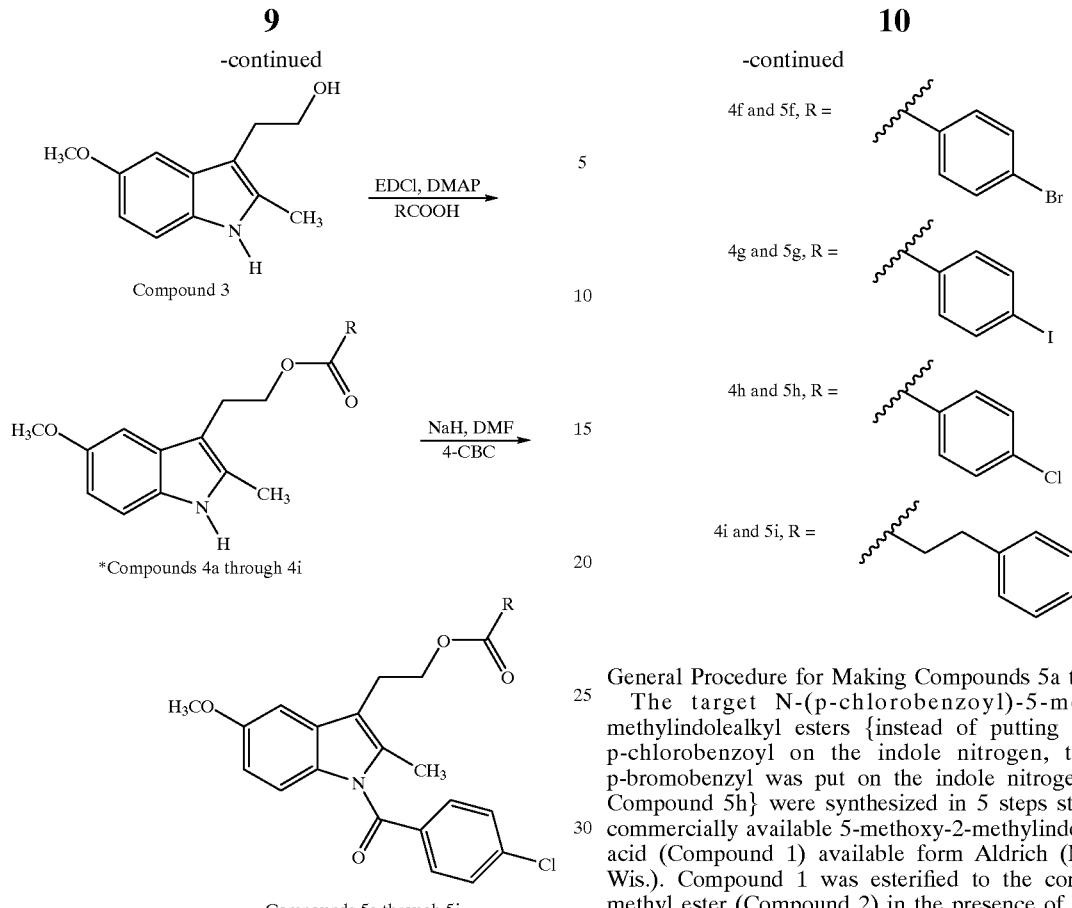

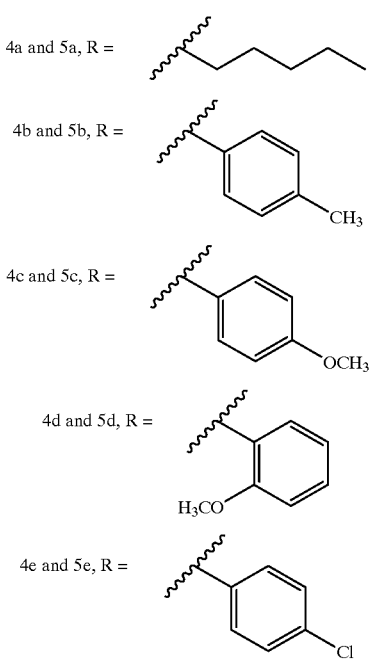

where:

4a and 5a, R =
4b and 5b, R =
4c and 5c, R =
4d and 5d, R =
4e and 5e, R =
4f and 5f, R =
4g and 5g, R =
4h and 5h, R =
4i and 5i, R =

General Procedure for Making Compounds 5a through 5i.

The target N-(p-chlorobenzoyl)-5-methoxy-2-methylindolealkyl esters {instead of putting the moiety p-chlorobenzoyl on the indole nitrogen, the moiety p-bromobenzyl was put on the indole nitrogen to make Compound 5h} were synthesized in 5 steps starting with commercially available 5-methoxy-2-methylindole-3-acetic acid (Compound 1) available form Aldrich (Milwaukee, Wis.). Compound 1 was esterified to the corresponding methyl ester (Compound 2) in the presence of MeOH and BOP-Cl. Reduction of Compound 2 to 5-methoxy-2-methylindole-3-ethanol (Compound 3) was accomplished with $LiBH_4$ in THF-MeOH. Use of $LiBH_4$ for reduction to an alcohol is discussed in Soai et al., "Mixed Solvents Containing Methanol as Useful Reaction Media for Unique Chemoselective Reductions with Lithium Borohydride", Vol. 51, *J. Org. Chem.*, pp. 4000–4005 (1986). Compound 3, which is an alcohol, served as the precursor in the syntheses of all target inventive esters. Initial attempts in the esterification of carboxylic acid derivatives employing BOP-CI or DCC as activating agents were unsuccessful. However, precursor esters (Compounds 4a through 4h) were prepared in good yields up to about 84% (and Compound 4i may be similarly prepared) when EDCI was used as the carboxylate activating agent, together with the appropriate RCOOH. Finally, N-acylation of the indole nitrogen in precursor ester Compounds 4a through 4h with 4-CBC (but with 4-BBBr for N-alkylation of Compound 4h into Compound 5h) in the presence of NaH afforded the final target inventive ester Compounds 5a through 5h (and like N-acylation may be employed to afford Compound 5i).

Possible Amide Preparation:

Instead of 5-methoxy-2-methylindole-3-ethanol (Compound 3), the corresponding amine is a known compound and could be easily synthesized or probably could be purchased, i.e., the OH moiety in Compound 3 instead would be an $NH_2$ moiety, so the starting material would be 5-methoxy-2-methylindole-3-ethyl amine, and then the rest of the reaction scheme would be followed to make the resultant amides with the same R moiety as the resultant ester Compounds 5a through 5i.

However, Compounds 9e and 9i were indeed made, using a reaction scheme starting with Compound 1, as discussed in general immediately below and in detail further below in Example II below.

The general reaction scheme for amide preparation of Compounds 9e, 9h, and 9i (which scheme also may be employed for amide preparation of Compounds 9a through 9d, 9f, and 9g) was as follows:

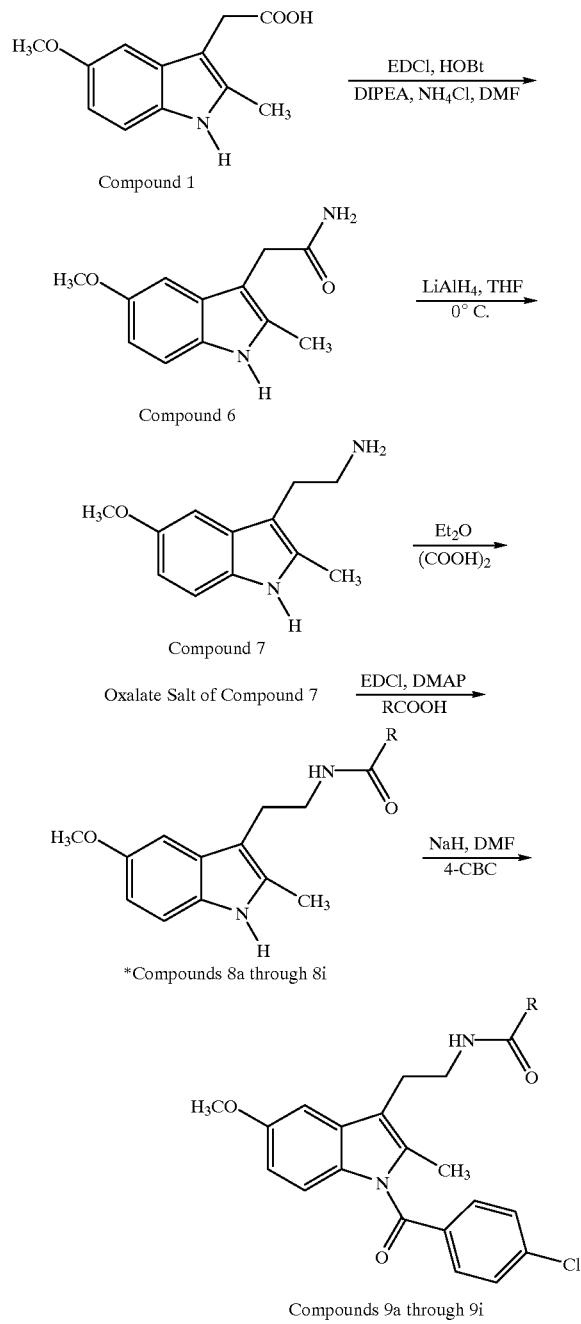

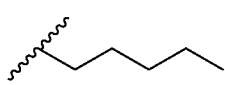

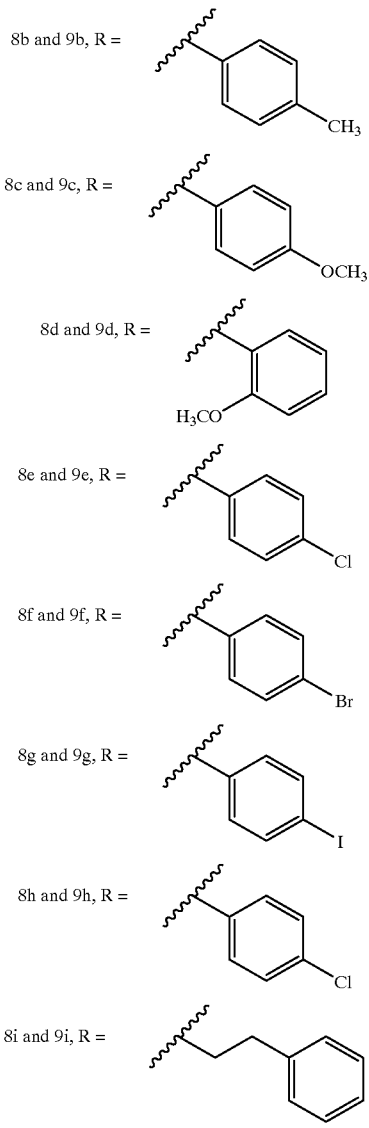

General Procedure for Making Compounds 9a through 9i.

The target N-(p-chlorobenzoyl)-5-methoxy-2-methylindolealkyl amides 9a through 9d and 9f through 9h may be synthesized in 5 steps starting with commercially available 5-methoxy-2-methylindole-3-acetic acid (Compound 1), available from Aldrich (Milwaukee, Wis.), as follows, and more specifically, the synthesis of the N-(p-chlorobenzoyl)-5-methoxy-2-methylindole-3-ethyl-(p-chloro) benzamide (Compound 9e), N-(p-bromobenzyl)-5-methoxy-2-methylindole-3-ethyl(p-chloro) benzamide (Compound 9h), and N-(p-chlorobenzoyl)-5-methoxy-2-methylindole-3-ethyl-(2-phenyl)ethylamide (Compound 9i) was achieved as follows.

Reaction of Compound 1 with ammonium chloride in the presence of EDCI, HOBt, and DIPEA afforded a primary amide (Compound 6). Such reactions of COOH to form $CONH_2$ are discussed in Wang et al., "A Selective Method for the Preparation of Primary Amides: Synthesis of Fmoc-L-4-Carboxamidophenylalanine and Other Compounds", Vol. 40, Tett. Lett., pp. 2501–2504 (1999). Lithium aluminum hydride reduction of Compound 6 afforded a primary amine (Compound 7) which was characterized, by treatment with $(COOH)_2$ and $Et_2O$, as its stable oxalate salt. EDCI-protected coupling of Compound 7 oxalate salt with the appropriate RCOOH (i.e., 4-chlorobenzoic acid in the event of Compound 8e) afforded a precursor amide (Compounds 8a through 8i), which upon N-acylation with 4-CBC (but with 4-BBBr for N-alkylation to make Compound 9h) in the presence of NaH and DMF furnished the target compounds 9a through 9i.

Treatment of Warm-blooded Vertebrate Animals:

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

More particularly, a treatment effective amount of the inventive ester or the inventive amide is administered to the warm-blooded vertebrate animal. Thus, the invention comprises administration of the ester or amide in concentrations calculated to provide the animal being treated with the appropriate milieu to provide an analgesic, antiinflammatory, or antipyretic effect.

The inventive ester and/or the inventive amide may be administered to the animal as a suppository or as a supplement to fluids that are administered internally or parenterally, for instance nutriment fluids such as intervenous sucrose solutions. Furthermore, intraoral (such as buccal or sublingual) administration or transdermal (such as with a skin patch) administration to the animal is also contemplated. A good discussion of intraoral administration can be seen in U.S. Pat. No. 4,229,447 issued Oct. 21, 1980 to Porter and U.S. Pat. No. 5,504,086 issued Apr. 2, 1996 to Ellinwood and Gupta. A good discussion of transdermal administration can be seen in U.S. Pat. No. 5,016,652 issued May 21, 1991 to Rose and Jarvik.

Additionally, administration to the animal may be by various oral methods, for instance as a tablet, capsule, or powder (crystalline form) that is swallowed. Also, oral administration may include that the inventive ester and/or the inventive amide is admixed in a carrier fluid appropriate therefor so that it is administered as a liquid (solution or suspension) that is drunk. When the ester and/or the amide is admixed in a carrier fluid, appropriate fluids include, but are not limited to, water, rehydration solutions (i.e., water with electrolytes such as potassium citrate and sodium chloride, for instance the solution available under the trade name RESOL® from Wyeth Laboratories), nutritional fluids (i.e., milk, fruit juice), and combinations thereof. Thus, the oral administration may be as a component of the diet, such as human food, animal feed, and combinations thereof.

In addition to oral administration such as by way of the mouth, contemplated also is administration of a solution or suspension to the esophagus, stomach, and/or duodenum, such as by gavage, i.e., by way of a feeding tube. Gavage type of administration is useful for when the animal is very ill and can no longer swallow food, medicine, et cetera, by mouth.

Hence, it is also contemplated that additional ingredients, such as various excipients, carriers, surfactants, nutriments, and the like, as well as various medicaments, other than the inventive ester and/or the inventive amide may be present, whatever the form that the ester and/or the amide is in. Medicaments other than an ester and/or an amide may include, but are not limited to, osmolytic polyols and osmolytic amino acids (i.e., myo-inositol, sorbitol, glycine, alanine, glutamine, glutamate, aspartate, proline, and taurine), cardiotonics (i.e., glycocyamine), analgesics, antibiotics, electrolytes (i.e., organic or mineral electrolytes such as salts), and combinations thereof.

A suitable dosing amount of inventive ester and/or inventive amide for administration to the animal should range from about 0.5 mg to about 7.0 mg per kg of body weight of the animal per day, more preferably from about 1.5 mg to about 6.0 mg per kg of body weight of the animal per day, and even more preferably from about 2.0 mg to about 5.0 mg per kilogram of body weight of the animal per day. Administration may be one or more times per day to achieve the total desired daily dose. Of course, the amount can vary depending on the severity of the illness and/or the age of the animal.

The present invention indicates that the inventive esters and the inventive amides process isozyme specificity for COX-2 and thus present an efficient strategy for the generation of potent and selective COX-2 inhibitors.

Laboratory Examples

The following is noted in connection with the materials and procedures below.

The inventive esters that were made and their selective COX-2 inhibition properties are listed in Table 1 below, and a total of 8 different N-acylated or N-alkylated esters were actually prepared and 1 is suggested. The inventive amides that may be made are listed in Table 2 below, and a total of 9 different N-acylated or N-alkylated amides are listed (and of these, Compounds 9e, 9h, and 9i were actually prepared as noted in Example II below).

Materials and Instruments

Arachidonic acid was purchased from Nu Chek Prep (Elysian, Minn.). [1-$^{14}$C]-arachidonic acid (~55–57 mCi/mmol) was purchased from NEN Dupont of American Radiolabeled Chemicals (ARC, St. Louis, Mo.). Hematin was purchased from Sigma Chemical Co. (St. Louis, Mo.). COX-1 was purified from ram seminal vesicles (Oxford Biomedical Research, Inc., Oxford, Mich.). The specific activity of the protein was 20 ($\mu MO_2$/min)/mg, and the percentage of holoprotein was 13.5%. ApoCOX-1 was prepared by reconstitution by the addition of hematin to the assay mixtures. Human COX-2 was expressed in SF-9 insect cells (GIBCO BRL) by means of the pVL 1393 expression vector (Pharmingen), and purified by ion-exchange and gel filtration chromatography. All of the purified proteins were shown by densitometric scanning of a 7.5% SDS PAGE gel to be >80% pure. Melting points were determined using a Gallenkamp melting point apparatus and were uncorrected. Chemical yields were unoptimized specific examples of one preparation. NSAIDs were purchased from Sigma (St. Louis, Mo.). All other chemicals were purchased from Aldrich (Milwaukee, Wis.). Methylene chloride was purchased as "anhydrous" from Aldrich and was used as received. All other solvents were HPLC grade. Analytical TLC (Analtech uniplates™) was used to follow the course of reactions. Silica gel (Fisher, 60–100 mesh) was used for column chromatography. $^1$H NMR and $^{13}$C NMR spectra in CDCl$_3$ were recorded on a Bruker WP-360 spectrometer or an AM-400 spectrometer; chemical shifts were expressed in parts per million (ppm, δ) relative to tetramethylsilane as an internal standard. Spin multiplicities were given as s (singlet), d (doublet), dd (doublet of doublets), t (triplet), q (quartet), and m (multiplet). Coupling constants (J) were reported in hertz (Hz). Positive ion electrospray ionization (ESI) and collision-induced dissociation (CID) mass spectra were obtained on a Finnigan TSQ 7000 mass spectrometer. CID fragmentations were consistent with assigned structures.

Time- and Concentration-Dependent Inhibition of ovine COX-1 and Human COX-2 Using the Thin Layer Chromatography (TLC) Assay.

Cyclooxygenase activity of ovine COX-1 (44 nM) or human COX-2 (88 nM) was assayed by TLC. Reaction mixtures of 200 μL consisted of hematin-reconstituted protein in 100 mM Tris-HCl, pH 8.0, 500 μM phenol, and [1-$^{14}$C]-arachidonic acid (50 μM, ~55–57 mCi/mmol). For the time-dependent inhibition assay, hematin-reconstituted COX-1 (44 nM) or COX-2 (88 nM) was preincubated at rt for 20 minutes with varying inhibitor concentrations in DMSO followed by the addition of [1-$^{14}$C]-arachidonic acid (50 μM) for 30 seconds at 37° C. Reactions were terminated by solvent extraction in Et$_2$O/CH$_3$OH/1 M citrate, pH 4.0 (30:4:1). The phases were separated by centrifugation at 2000 g for 2 minutes and the organic phase was spotted on a TLC plate available from J. T. Baker (Phillipsburg, N.J.). The plate was developed in EtOAc/CH$_2$Cl$_2$/glacial AcOH (75:25:1) at 4° C. Radiolabeled prostanoid products were quantitatively determined with a radioactivity scanner available from Bioscan, Inc. (Washington, D.C.). The percentage of total products observed at different inhibitor concentrations was divided by the percentage of products observed for protein samples preincubated for the same time with DMSO.

Enzymology.

IC$_{50}$ values for the inhibition of purified human COX-2 or ovine COX-1 by test compound were determined by the TLC assay. HoloCOX-2 (66 nM) or holoCOX-1 (44 nM) in 100 mM Tris-HCl, pH 8.0, containing 500 μM phenol, was treated with several concentrations of inhibitors at 25° C. for 20 min. Since the recombinant COX-2 had a lower specific activity than ovine COX-1, the protein concentrations were adjusted such that the percentages of total products obtained following catalysis of arachidonic acid by the two isoforms were comparable. The cyclooxygenase reaction was initiated by the addition of [1-$^{14}$C]-arachidonic acid (50 μM) at 37° C. for 30 seconds. Control experiments in the absence of inhibitor indicated ~25–30% conversion of fatty acid substrate to products which was sufficient for assessing the inhibitory properties of all test compounds described in this study. Under these conditions, indomethacin (comparison) displayed selective time- and concentration-dependent inhibition of COX-1 [(IC$_{50}$ (COX-1)~0.05 μM; IC$_{50}$ (COX-2) ~0.75 μM)], and NS-398 (comparison) displayed selective COX-2 inhibition [NS-398: IC$_{50}$ (COX-2) ~0.12 μM; IC$_{50}$ (COX-1)>66 μM].

EXAMPLE I

Procedure for Preparation of Target Inventive Ester Compounds 5a Through 5i

Preparation of the Alcohol (Compound 3)

A reaction mixture containing 5-methoxy-2-methylindole-3-acetic acid (Compound 1, 800 mg, 3.64 mmol) and BOP-Cl (926 mg, 3.64 mmol) in 10 mL of anhydrous CH$_2$Cl$_2$ was treated with Et$_3$N (735 mg, 7.28 mmol) and allowed to stir at rt for 5 minutes. The mixture was then treated with anhydrous MeOH (0.5 mL) and stirred overnight at rt. Following dilution with CH$_2$Cl$_2$ (30 mL), the organic solution was washed with water (2×25 mL), dried (MgSO$_4$), filtered, and the solvent concentrated in vacuo. The crude esterified resultant (Compound 2) was purified by chromatography on silica gel (EtOAc:hexanes; 25:75) to afford a pale yellow oil (648 mg, 76%). $^1$H NMR (CDCl$_3$) δ 7.75 (bs, 1 H, NH), 7.13–7.16 (d, 1 H, J=8.7 Hz, ArH), 6.98–6.99 (d, 1 H, J=2.2 Hz, ArH), 6.75–6.79 (dd, 1 H, J=8.7 Hz & 2.3 Hz, ArH), 3.85 (s, 3 H, OCH$_3$), 3.66 (s, 2 H, CH$_2$), 2.39 (s, 3 H, CH$_3$).

Next, a reaction mixture containing 5-methoxy-2-methylindole-3-(methyl)acetate (Compound 2,648 mg, 2.78 mmol) in anhydrous ether (20 mL) and dry MeOH (150 μL) was treated with LiBH$_4$ (122 mg, 5.6 mmol) at 0° C. The reaction mixture was allowed to attain rt and stirred at that temperature for 5 hours. The mixture was diluted with water and extracted with ether (2×30 mL). The combined organic solution was washed with water (2×25 mL), dried (MgSO$_4$), filtered, and the solvent concentrated in vacuo. The crude alcohol, namely 5-methoxy-2-methylindole-3-ethanol (Compound 3), was purified by recrystallization in CH$_2$Cl$_2$/hexanes to afford white needles (384 mg, 67%). The mp=102–103° C. (It is noted that Archibald et al., "Synthesis and Hypotensive Activity of Benzamidopiperidylethylindoles", Vol. 14, J. Med. Chem., pp. 1054–1059 (1971) indicated the mp=98–101° C. $^1$H NMR (CDCl$_3$) δ 7.72 (bs, 1 H, NH), 7.15–7.18 (d, 1 H, J=8.7 Hz, ArH), 6.97–6.98 (d, 1 H, J=2.3 Hz, ArH), 6.76–6.80 (dd, 1 H, J=8.7 Hz & 2.3 Hz, ArH), 3.83–3.85 (m, 5 H, CH$_2$ & OCH$_3$), 2.92–2.97 (t, 2 H, J=6.4 Hz, CH$_2$), 2.39 (s, 3 H, CH$_3$).

Procedure for the Esterifcation of Compound 3
(Preparation of Compounds 4a Through 4i)

To a solution of the appropriate carboxylic acid RCOOH (2.18 mmol) in 5 mL of anhydrous CH$_2$Cl$_2$ was added EDCI (2.44 mmol), DMAP (0.244 mmol) and Compound 3 (2.44 mmol) after which the reaction mixture was stirred overnight at rt. Upon dilution with water, the aqueous solution was extracted with CH$_2$Cl$_2$ (2×20 mL). The combined organic was washed with water (2×25 mL), dried (MgSO$_4$), filtered, and the solvent concentrated in vacuo. The residue was chromatographed on silica gel (EtOAc:hexanes; 10:90–25:75) to afford precursor ester Compounds 4a through 4h (and could afford Compound 4i), which were used in the next step (namely, N-acylation or N-alkylation of the indole nitrogen) without any further purification, owing to their unstable nature.

(Compound 4a) 5-methoxy-2-methylindole-3-ethyl-(4-pentyl) valerate was obtained as a pale yellow solid upon chromatography on silica gel. As Compound 4a was unstable, NMR characterization was not performed, and instead, Compound 4a was used directly in the next step for preparation of Compound 5a.

(Compound 4b) 5-methoxy-2-methylindole-3-ethyl-(4-methylphenyl) benzoate was obtained as a pale yellow solid upon chromatography on silica gel (EtOAc:hexanes; 10:90) in 59% yield. $^1$H NMR (DMSO-d$_6$) δ 10.59 (bs, 1 H, NH), 7.73–7.76 (d, 1 H, J=6.7 Hz & 1.8 Hz, ArH), 7.30–7.44 (m, 1 H, ArH), 7.23–7.30 (m,2 H, ArH), 7.08–7.11 (d, 1 H, J=8.7 Hz, ArH), 6.96–6.97 (d, 1 H, J=2.0 Hz, ArH), 6.58–6.62 (dd, 1 H, J=8.7 Hz & 2.3 Hz, ArH), 4.33–4.37 (t, 2 H, J=6.8 Hz, CH$_2$), 3.67 (s, 3 H, OCH$_3$), 3.01–3.05 (t, 2 H, J=6.8 Hz, CH$_2$), 2.44 (s, 3H, CH$_3$), 2.29 (s, 3 H, CH$_3$).

(Compound 4c) 5-methoxy-2-methylindole-3-ethyl-(4-methoxyphenyl) benzoate was obtained as a bright yellow oil upon chromatography on silica gel (EtOAc:hexanes; 20:80) in 84% yield. $^1$H NMR (CDCl$_3$) δ 7.60–7.99 (m, 4 H, ArH), 7.39 (s, 1 H, NH), 7.15–7.17 (d, 2 H, J=8.7 Hz, ArH), 7.02–7.03 (d, 1 H, J=2.1 Hz, ArH), 6.88–6.91 (d, 1 H, J=9.0 Hz, ArH), 6.75–6.79 (dd, 1 H, J=8.7 Hz & 2.1 Hz, ArH), 4.42–4.47 (t, 2 H, J=7.2 Hz, CH$_2$),3.83 (s, 3 H, OCH$_3$), 3.70 (s, 3 H, OCH3), 3.09–3.14 (t, 2 H, J=7.2 Hz, CH$_2$), 2.40 (s, 3 H, CH$_3$).

(Compound 4d) 5-methoxy-2-methylindole-3-ethyl-(2-methoxyphenyl) benzoate was obtained as a pale yellow solid upon chromatography on silica gel. As Compound 4d was unstable, NMR characterization was not performed, and instead, Compound 4d was used directly in the next step for preparation of Compound 5d.

(Compound 4e) 5-methoxy-2-methylindole-3-ethyl-(4-chlorophenyl)-benzoate was obtained as a white solid upon chromatography on silica gel (EtOAc:hexanes; 10:90) in 73% yield. mp=119–120° C.; $^1$H NMR (CDCl$_3$) d 7.92–7.97 (d, 2 H, J=6.7 Hz & 1.8 Hz, ArH), 7.70 (bs, 1 H, NH), 7.37–7.41 (d, 2 H, J=6.8 Hz & 1.9 Hz, ArH), 7.14–7.19 (d, 1 H, J=8.7 Hz, ArH), 7.01–7.02 (d, 1 H, J=2.0 Hz, ArH), 6.75–6.80 (dd, 1 H, J=8.7 Hz & 2.3 Hz, ArH), 4.43–4.51 (t, 2 H, J=7.2 Hz, CH$_2$), 3.83 (s, 3 H, OCH$_3$), 3.09–3.16 (t, 2 H, J=7.2 Hz, CH$_2$), 2.39 (s, 2 H, CH$_3$).

(Compound 4f) 5-methoxy-2-methylindole-3-ethyl-(4-bromophenyl) benzoate was obtained as a pale yellow solid upon chromatography on silica gel (EtOAc:hexanes; 5:95) in 72% yield. mp=122–123° C.; $^1$H NMR (CDCl$_3$) d 7.92–7.97 (d, 2 H, J=6.7 Hz & 1.8 Hz, ArH), 7.70 (bs, 1 H, NH), 7.37–7.41 (d, 2 H, J=6.8 Hz & 1.9 Hz, ArH), 7.14–7.19 (d, 1 H, J=8.7 Hz, ArH), 7.01–7.02 (d, 1 H, J=2.0 Hz, ArH), 6.75–6.80 (dd, 1 H, J=8.7 Hz, ArH), 4.43–4.51 (t, 2 H, J=7.2 Hz, CH$_2$),3.83 (s, 3 H, OCH$_3$), 3.09–3.16 (t, 2 H, J=7.2 Hz, CH$_2$), 2.40 (s, 3 H, CH$_3$).

(Compound 4g) 5-methoxy-2-methylindole-3-ethyl-(4-iodophenyl) benzoate was obtained as a pale yellow solid upon chromatography on silica gel (EtOAc:hexanes; 5:95) in 71% yield. mp=131–132° C.; $^1$H NMR (CDCl$_3$) d 7.73–7.76 (m, 4 H, ArH), 7.14–7.19 (d, 1 H, J=8.7 Hz, ArH), 7.01–7.02 (d, 1 H, J=2.0 Hz, ArH), 6.75–6.80 (dd, 1 H, J=8.7 Hz & 2.3 Hz, ArH), 4.43–4.51 (t, 2 H, J=7.2 Hz, CH$_2$), 3.83 (s, 3 H, OCH$_3$), 3.09–3.16 (t, 2 H, J=7.2 Hz, CH$_2$), 2.39(s, 3 H, CH$_3$).

(Compound 4h) Same as Compound 4e.

(Compound 4i) 5-methoxy-2-methylindole-3-ethyl-(2-phenyl)acetate. This may be similarly obtained and characterized by NMR.

Procedure for N-acylation (or N-alkylation to make Compound 5h) of Precursor Ester Compounds 4a through 4i (Preparation of Target Ester Compounds 5a Through 5i)

To a solution of the appropriate ester (1.57 mmol) in 5 mL of anhydrous DMF was added NaH (1.88 mmol) at 0° C. under argon. The reaction mixture was stirred at 0° C. for 20 minutes and then treated with 4-CBC (1.88 mmol) for N-acylation of the indole nitrogen, except 4-BBBr was used for N-alkylation of the indole nitrogen to prepare Compound 5h. The reaction mixture was stirred overnight and then diluted with water. The aqueous solution was extracted with ether (2×20 mL). The combined organic was washed with water (2×25 mL), dried (MgSO$_4$), filtered, and the solvent concentrated in vacuo. The residue was chromatographed on silica gel (EtOAc:hexanes; 5:95–10:90) to afford the inventive ester target Compounds 5a through 5h (and Compound 5i may be similarly prepared).

(Compound 5a) N-(p-chlorobenzoyl)-5-methoxy-2-methylindole-3-ethyl-valerate was obtained as a colorless oil in 34% yield. $^1$H NMR (CDCl$_3$) δ 7.47–7.50 (d, 2 H, J=8.4 Hz, ArH), 7.29–7.32 (d, 2 H, J=8.4 Hz, ArH), 6.80–6.81 (d, 1 H, J=2.4 Hz, ArH), 6.68–6.71 (d, 1 H, J=9.0 Hz ArH), 6.48–6.51 (d, 1 H, J=8.9 Hz, ArH), 4.07–4.11 (t, 2 H, J=7.2 Hz, CH$_2$), 3.66–3.71 (s, 3 H, CH$_3$), 2.80–2.85 (t, 2 H, J=7.2 Hz, CH$_2$), 2.21 (s, 3 H, CH$_3$), 2.10–2.15 (t, 2 H, J=7.2 Hz, CH$_2$), 1.39–1.46 (m, 4 H, CH$_2$), 0.70–0.76 (t, 3 H, CH$_3$).

(Compound 5b) N-(pchlorobenzoyl)-5-methoxy-2-methylindole-ethyl-(p-methyl)benzoate was obtained as a fluffy white solid upon recrystallization with CH$_2$Cl$_2$/hexanes in 31% yield. mp=127–128° C.; $^1$H NMR (CDCl$_3$) δ 7.83–7.86 (d, 1 H, J=8.7 Hz, ArH), 7.62–7.65 (d, 2 H, J=8.4 Hz, ArH), 7.37–7.45 (m, 3 H, ArH), 7.19–7.26 (m, 2 H, ArH), 7.00–7.01 (d, 1 H, J=2.2 Hz, ArH), 6.90–6.93 (d, 1 H, J=Hz, ArH), 6.65–6.69 (dd, 1 H, J=8.9 Hz & 2.3 Hz, ArH), 4.474.52 (t, 2 H, J=6.9 Hz, CH$_2$), 3.80 (s, 3 H, OCH$_3$), 3.11–3.15 (t, 2 H, J=6.9 Hz, CH$_2$), 2.56 (s, 3 H, CH$_3$), 2.36 (s, 3 H, CH$_3$). ESI-CID 462 (MH$^+$), m/z 326, 139.

(Compound 5c) N-(p-chlorobenzoyl)-5-methoxy-2-methylindole-3ethylo-(p-methoxy)benzoate was obtained as a pale yellow solid upon recrystallization with CH$_2$Cl$_2$/hexanes in 28% yield. mp=95–97° C.; $^1$H NMR (CDCl$_3$) δ 7.95–7.97 (d, 2 H, J=8.7 Hz, ArH), 7.62–7.64 (d, 2 H, J=8.4 Hz, ArH), 7.42–7.44 (d, 2 H, J=8.3 Hz, ArH), 7.01–7.02 (d, 1 H, J=2.2 Hz, ArH), 6.89–6.93 (m, 3 H, ArH), 6.66–6.69 (dd, 1 H, J=8.9 Hz & 2.3 Hz, ArH), 4.47–4.51 (t, 2 H, J=6.9 Hz, CH$_2$), 3.86 (s, 3 H, OCH$_3$), 3,82 (s, 3 H, OCH$_3$), 3.10–3.14 (t, 2 H, J=6.9 Hz, CH$_2$), 2.36 (s, 3 H, CH$_3$). ESI-CID 478 (MH$^+$), m/z 326, 308, 188, 139.

(Compound 5d) N-(pchlorobenzoyl)-5-methoxy-2-methylindole-3thyl-(o-methoxy)benzoate was obtained as a white solid upon recrystallization with CH$_2$Cl$_2$/hexanes in 28% yield. mp=88–90° C.; $^1$H NMR (CDCl$_3$) δ 7.95–7.97 (d, 2 H, J=8.7 Hz, ArH), 7.62–7.66 (m, 2 H, ArH), 7.41–7.45 (m, 3 H, ArH), 6.89–7.01 (m, 5 H, ArH), 6.66 6.69 (dd, 1 H, J=8.9 Hz & 2.3 Hz, ArH), 4.47–4.51 (t, 2 H, J=6.9 Hz, CH$_2$), 3.87 (s, 3 H, OCH$_3$), 3.80 (s, 3 H, OCH$_3$), 3.10–3.14 H, J=6.9 Hz, CH$_2$), 2.36 (s, 3 H, CH$_3$). ESI-CID 478 (MH$^+$), m/z 326, 139.

(Compound 5e) N -(p-chlorobenzoyl)-5-methoxy-2-methylindole-3-ethyl-(p-chloro)benzoate was obtained as a pale yellow solid upon recrystallization with CH$_2$Cl$_2$/hexanes in 35% yield. mp=102–104° C.; $^1$H NMR (CDCl$_3$) δ 7.91–7.96 (d, 2 H, J=8.5 Hz, ArH), 7.62–7.66 (d, 2 H, J=8.5 Hz, ArH), 7.38–7.46 (m, 4 H, ArH), 7.00–7.01 (d, 1 H, J=2.3 Hz, ArH), 6.86–6.91 (d, 1 H, J=9.0 Hz, ArH), 6.66–6.70 (dd, 1 H, J=9.0 Hz & 2.4 Hz, ArH), 4.47–4.54 (t, 2 H, J=7.0 Hz, CH$_2$), 3.82 (s, 3 H, OCH$_3$),3.10–3.17 (t, 2 H, J=7.0 Hz, CH$_2$), 2.38 (s, 3 H, CH$_3$). ESI-CID 482 (MH$^+$), 326, 188, 139.

(Compound 5f) N-(p-Chlorobenzoyl)-5-methoxy-2-methylindole-3-ethyl-(p-bromo)benzoate was obtained as a pale yellow solid upon recrystallization with CH$_2$Cl$_2$/hexanes in 41% yield. mp=97–99° C.; $^1$H NMR (CDCl$_3$) δ 7.84–7.88 (m, 3 H, ArH), 7.54–766 (m, 3 H, ArH), 7.42–7.46 (m, 2 H, ArH), 6.99–7.00 (d, 1 H, J=2.4 Hz, ArH), 6.86–6.91 (d, 1 H, J=9.0 Hz, ArH), 6.69–6.70 (dd, 1 H, J=9.0 Hz & 2.4 Hz, ArH), 4.47–4.54 (t, 2 H, J=7.0 Hz, CH$_2$), 3.82 (s, 3 H, OCH$_3$), 3.09–3.16 (t, 2 H, J=7.0 Hz, CH$_2$), 2.37 (s, 3 H, CH$_3$).

(Compound 5g) N-(phlorobenzoyl)-5-methoxy-2-methylindole-3-ethyl(-p-iodo)benzoate was obtained as a pale yellow solid upon recrystallization with CH$_2$Cl$_2$/hexanes in 40% yield. mp=128–129° C.; $^1$H NMR (CDCl$_3$) δ 7.84–7.88 (m, 3 H, ArH), 7.54–7.66 (m, 3 H, ArH), 7.42–7.46 (m, 2 H, ArH), 6.99–7.00 (d, 1 H, J=2.4 Hz, ArH), 6.86–6.91 (d, 1 H, J=9.0 Hz, ArH), 6.69–6.70 (dd, 1 H, J=9.0 Hz & 2.4 Hz, ArH), 4.47–4.54 (t, 2 H, J=7.0 Hz, CH$_2$), 3.82 (s, 3 H, OCH$_3$), 3.09–3.16 (t, 2 H, J=7.0 Hz, CH$_2$), 2.37 (s, 3 H, CH$_3$).

(Compound 5h) N-(p-bromobenzyl)-5-methoxy-2-methylindole-3-ethyl-(p-chloro)benzoate was obtained as a white solid upon recrystallization with CH$_2$Cl$_2$/hexanes in 14% yield. mp=96–98° C.; $^1$H NMR (CDCl$_3$) δ 7.89–7.93 (d, 2 H, J=9.0 Hz, ArH), 7.33–7.38 (m, 4 H, ArH), 7.04–7.07 (d, 1 H, J=9.0 Hz, ArH), 6.76–6.79 (dd, 1 H, J=9.0 Hz & 2.1 Hz, ArH), 5.20 (s, 2 H, CH$_2$), 4.46–4.51 (t, 2 H, J=7.0 Hz, CH$_2$), 3.82 (s, 3 H, OCH$_3$), 3.14–3.19 (t, 2 H, J=7.0 Hz, CH$_2$), 2.24 (s, 3 H, CH$_3$). ESI-CID 512 (MH$^+$), m/z 358, 187, 171.

(Compound 5i) N-(p-chlorobenzoyl)-5-methoxy-2-methylindole-3-ethyl-(2-phenyl)acetate may be similarly obtained.

The structures and IC$_{50}$ values for inventive target Compounds 5a through 5i are set out in Table 1 below.

TABLE 1

Selective COX-2 Inhibition by Inventive Esters

| Compound | IC$_{50}$ (μM) | | |
| --- | --- | --- | --- |
| | COX-2 | COX-1 | Selectivity |
| 5a 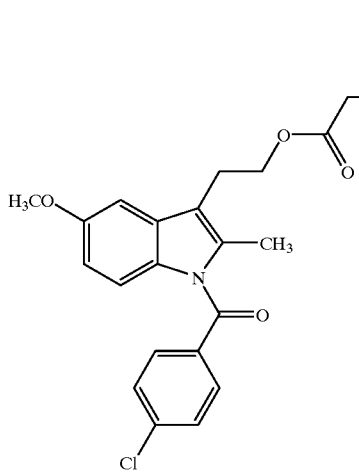 | 0.65 | >66 | >1015 |
| 5b 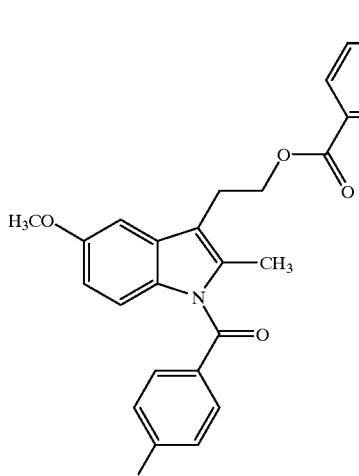 | 0.05 | >66 | >1320 |

TABLE 1-continued
Selective COX-2 Inhibition by Inventive Esters
| Compound | | IC$_{50}$ ($\mu$M) | | |
| --- | --- | --- | --- | --- |
| | | COX-2 | COX-1 | Selectivity |
| 5c | 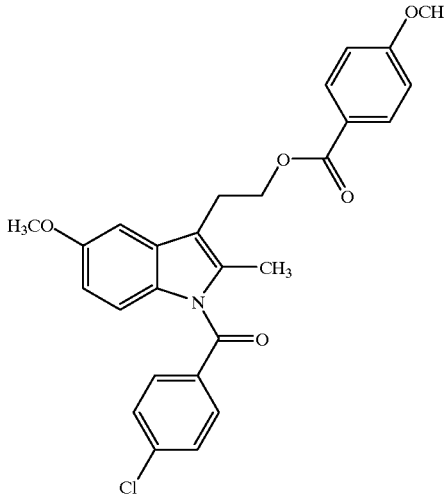 | 0.04 | >66 | >1466 |
| 5d | 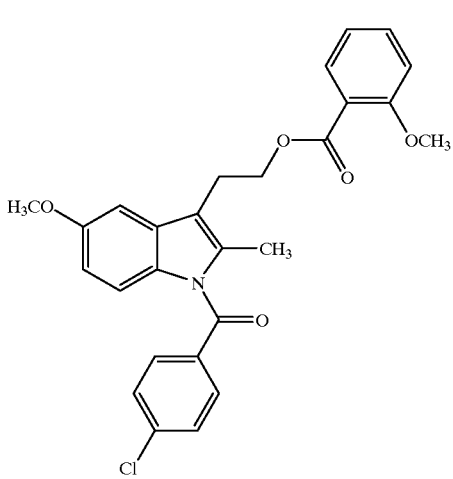 | 0.05 | >66 | >1320 |
| 5e | 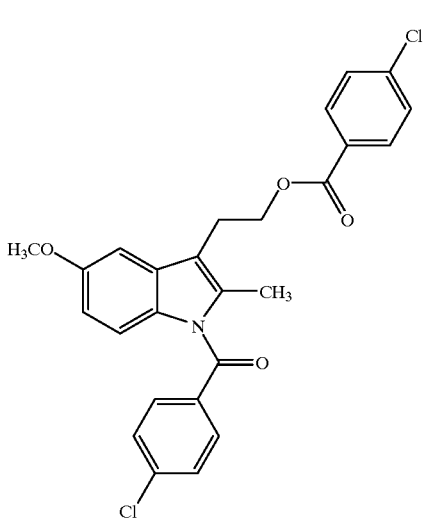 | 0.05 | >66 | >1320 |

TABLE 1-continued
Selective COX-2 Inhibition by Inventive Esters
| Compound | | IC$_{50}$ ($\mu$M) | | |
|---|---|---|---|---|
| | | COX-2 | COX-1 | Selectivity |
| 5f | 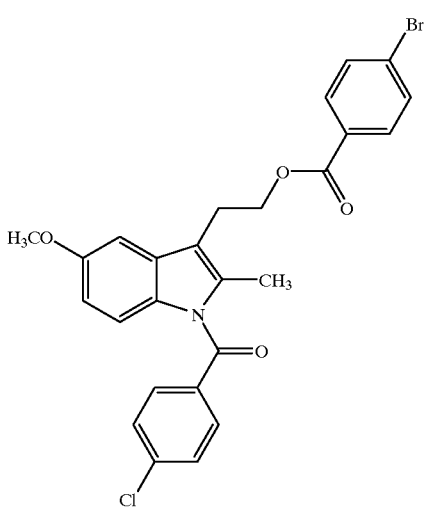 | 0.04 | >66 | >1466 |
| 5g | 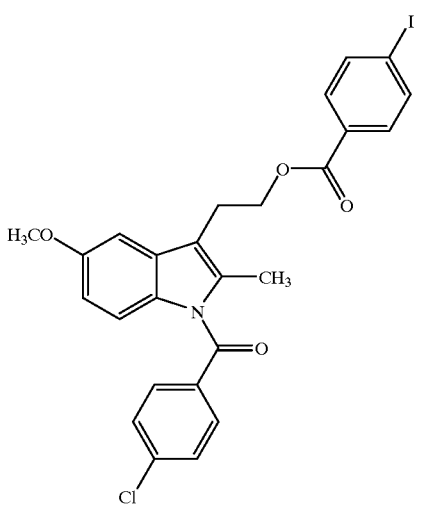 | 0.05 | >66 | >1320 |

TABLE 1-continued

Selective COX-2 Inhibition by Inventive Esters

| | | IC$_{50}$ ($\mu$M) | | |
| --- | --- | --- | --- | --- |
| Compound | | COX-2 | COX-1 | Selectivity |
| 5h | | <2.0 | >66 | >33 |
| 5i | | not prepared | | |

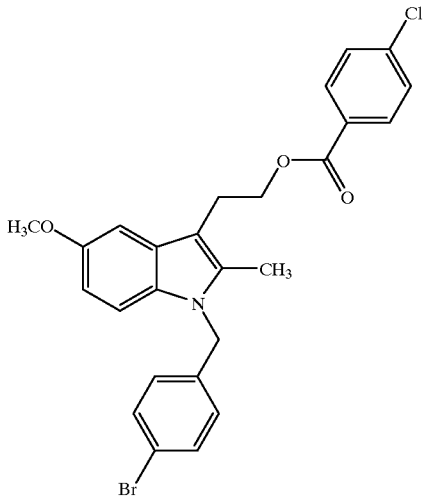

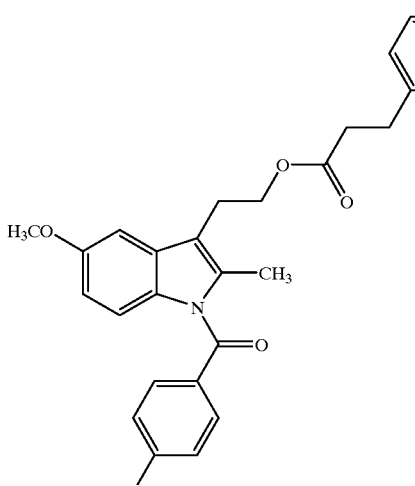

IC$_{50}$ values represent time-dependent inhibition. Ovine COX-1 (44 nM) was preincubated with inhibitors at 25° C. for 15 min followed by the addition of [1-$^{14}$C]-arachidonic acid (50 $\mu$M) at 37° C. for 30 seconds. All assays were conducted in duplicate.

As can be seen in Table 1, all of the N-(p-chlorobenzoyl)-5-methoxy-2-methylindole-3-ethyl ester Compounds 5a through 5g and the N-(p-bromobenzyl)-5-methoxy-2-methyl-3-ethyl ester Compound 5h displayed potent and selective inhibition of COX-2. These compounds exhibited IC$_{50}$ values for COX-2 inhibition in the low nanomolar range with very high COX-2 selectivity ratios.

Example II

Procedure for Preparation of Target Inventive Amide Compounds 9a through 9i

The structures for suggested Compounds 9a through 9d and 9f through 9h, and also, the structures for Compounds 9e, 9h, and 9i, which were made, are set out in Table 2 below.

TABLE 2

(Suggested Amides 9a through 9d and 9f
through 9h, and Actually Made Amides 9e, 9h, and 9i)

Compound 9a, 9b, 9c, 9d, 9e, 9f

TABLE 2-continued (Suggested Amides 9a through 9d and 9f through 9h, and Actually Made Amides 9e, 9h, and 9i)

| Compound | |
|---|---|
| 9g | (structure: 5-methoxy-2-methylindole with N-CH₂CH₂-NH-C(=O)-C₆H₄-I at 3-position and N-C(=O)-C₆H₄-Cl on indole N) |
| 9h | (structure: 5-methoxy-2-methylindole with N-CH₂CH₂-NH-C(=O)-C₆H₄-Cl at 3-position and N-CH₂-C₆H₄-Br on indole N) |
| 9i | (structure: 5-methoxy-2-methylindole with N-CH₂CH₂-NH-C(=O)-CH₂CH₂-C₆H₅ at 3-position and N-C(=O)-C₆H₄-Cl on indole N) |

Preparation of 5-methoxy-2-methylindole-3-acetamide (Compound 6)

A reaction mixture containing Compound 1 (880 mg, 4.02 mmol), EDCl (1.16 g, 6.04 mmol), HOBt (816 mg, 6.04 mmol), DIPEA (2.8 mL, 16.08 mmol), ammonium chloride (430 mg, 8.04 mmol) in anhydrous DMF 16 mL (4 mL DMF/1 mmol) was stirred at rt for 5 hours. The reaction was diluted with water and extracted with EtOAc (3×10 mL). The combined EtOAc extracts were washed with saturated NaHCO$_3$ (2×10 mL), water, dried (MgSO$_4$), filtered, and the solvent concentrated in vacuo till a minimum volume of EtOAc remained. Upon cooling, the desired primary amide crystallized out as a white crystalline solid, in 64% yield. mp=146–148° C. t is noted that Shaw, "The Synthesis of Tryptamines Related to Seratonin", Vol. 77, *J. Amer. Chem. Soc.*, pp. 4319–4324 (1955) reported the mp=147–150° C. $^1$H NMR (DMSO-d$_6$) δ 10.56 (s, 1 H, NH), 7.34 (bs, 1 H, CONH), 6.96–7.22 (m, 1 H, ArH), 6.81 (s, 1 H, ArH), 6.74 (bs, 1 H, CONH), 6.58–6.62 (m, 1 H, ArH), 3.78 (s, 3 H, CH$_3$), 3.34 (s, 2 H, CH$_2$), 2.29 (s, 3 H, CH$_3$). ESI-CID 219 (MH$^+$), m/z 187, 174, 148.

Preparation of 5-methoxy-2-methylindole-3-ethyl amine (Compound 7)

To a suspension of LiAH$_4$ (370 mg, 9.74 mmol) in anhydrous THF (80 mL) was added 5-methoxy-2-methylindole-3-acetamide (Compound 6) (760 mg, 3.38 mmol) under argon at 0° C. The reaction mixture was allowed to stir at rt under argon for 60 hours. The reaction was carefully quenched by the addition of ice-cold water (~100 mL) and then extracted with Et$_2$O (3×25 mL). The combined ether extracts were washed with 1 N HCl (2×25 mL). The combined acidic extract was washed once with Et$_2$O (50 mL) and then neutralized with 1 N NaOH. Following neutralization, the aqueous solution was extracted with Et$_2$O (3×25 mL). The combined organic solution was washed with water, dried (MgSO$_4$), filtered, and the solvent concentrated in vacuo to afford a yellow oil (530 mg, 73%). A portion of the oil was treated with a solution containing one equivalent of oxalic acid in Et$_2$O to furnish the oxalate salt of Compound 7, which was recrystallized from MeOH/Et$_2$O to afford a light brown crystalline solid. mp=176–178° C.; $^1$H NMR (CD$_3$OD) δ 7.12–7.16 (d, 1 H, J=8.7 Hz, ArH), 6.94–6.95 (d, 1 H, J=2.3 Hz, ArH), 6.67–6.71 (dd, 1 H, J=8.7 & 2.3 Hz, ArH), 3.80–3.84 (s, 3 H, OCH$_3$), 3.01–3.11 (dd, 4 H, J=8.3 Hz, CH$_2$), 2.36 (s, 3 H, CH$_3$). ESI-CID 205 (MH$^+$), m/z 188, 173, 158, 145, 130.

Preparation of N-(p-chlorobenzoyl)-5-methoxy-2-methylindole-3-ethyl-(p-chloro)benzamide (Compound 9e)

A reaction mixture containing Compound 7 oxalate salt (520 mg, 2.55 mmol), EDCl (489 mg, 2.55 mmol), DMAP (31 mg, 0.255 mmol), and 4-chlorobenzoic acid (354 mg, 2.26 mmol) in anhydrous methylene chloride (15 mL) was stirred at rt for 3 hours. The reaction mixture was diluted with water and extracted with CH$_2$Cl$_2$ (2×15 mL). The combined CH$_2$Cl$_2$ extracts were washed with water, dried (MgSO$_4$), filtered, and the solvent concentrated in vacuo. The crude amide was chromatographed on silica gel (EtOAc:hexanes; 25:75 then 60:40) to afford the precursor amide Compound 8e as a yellow oil (390 mg, 45%), which was used in the next step without any further characterization owing to its unstable nature.

To a reaction mixture comprising Compound 8e (390 mg, 1.14 mmol) in anhydrous DMF (3 mL) was added sodium hydride (60% dispersion in mineral oil) (56 mg, 1.4 mmol) at 0° C. under argon. After stirring for 20 minutes, the reaction was treated with 4-CBC (180 µL, 1.4 mmol) for N-acylation of the indole nitrogen, and the reaction was allowed to stir overnight at rt. The reaction mixture was quenched with water and extracted with $Et_2O$ (3×10 mL). Th combined $Et_2O$ extracts were washed with saturated $NaHCO_3$ (3×10 mL), water, dried ($MgSO_4$), filtered, and the solvent concentrated in vacuo to afford a yellow residue. Silica gel chromatography (EtOAc:hexanes; 20:80 then 40:60) afforded the desired product as a pale yellow solid (recrystallized from EtOAc/hexanes) (371 mg, 67%). mp=165–166° C.; $^1H$ NMR ($CDCl_3$) δ 7.58–7.65 (m, 4 H, ArH), 7.43–7.47 (d, 2 H, J=8.6 Hz, ArH), 7.36–7.39 (d, 2 H, J=8.6 Hz, ArH), 6.96–6.97 (d, 1 H, J=2.4 Hz, ArH), 6.88–6.90 (d, 1 H, J=9.0 Hz, ArH), 6.65–6.69 (dd, 1 H, J=9.0 & 2.5 Hz, ArH), 6.17 (bt, 1 H, CONH), 3.76 (s, 3 H, $OCH_3$), 3.67–3.71 (q, 2 H, J=6.6 Hz, $CH_2$), 2.99–3.04 (t, 2 H, J=6.75 Hz, $Ch_2$), 2.33 (s, 3 H, $CH_3$).

Preparation of N-(p-chlorobenzyl)-5-methoxy-2-methylindole-3-ethyl-(p-chloro)benzamide (Compound 9h)

The procedure employed for preparation of Compound 9e was repeated except as follows. In the treatment of Compound 8e, 4-bromobenzyl bromide for N-alkylation was used instead of 4-CBC for N-acylation, so the resultant was 9h instead of 9e.

Preparation of N-(p-chlorobenzoyl)-5-methoxy-2-methylindole-3-ethyl-(2-phenyl)ethylamide (Compound 9i)

The procedure employed for preparation of Compound 9e was repeated except as follows. In the treatment of Compound 7, phenylacetic acid was used instead of 4-chlorobenzoic acid, so the resultant was 8i instead of 8e.

Then, 8i was treated the same as 8e to afford 9i instead of 9e.

The $IC_{50}$ value for inventive target Compounds 9e and 9i were determined to be as follows.

| Selective COX-2 Inhibition by Inventive Amide | | | |
|---|---|---|---|
| | $IC_{50}$ (µM) | | |
| Compound | COX-2 | COX-1 | Selectivity |
| 9e | 0.050 | 4.0 | 80 |
| 9h | 0.040 | >66 | >1650 |
| 9i | ~0.040 | ~17 | ~425 |

Example III

Carrageenan-Induced Rat Foot Paw Edema Assay for Ester Compound 5c and Amide Compound 9e as Inhibitor All procedures were performed according to approved animal protocols (#M/98/251, Vanderbilt University Animal Care Committee). Male Sprague Dawley rats (Harlan Sprague Dawley, Indianapolis, Ind.) (150–175 grams) were fasted for 18 hours and then injected with λ-carrageenan (0.1 ml of a 1% suspension in 0.85% saline, Fluka BioChemika, Milwaukee, Wis.) into the right hind footpad. After 1 hour, 90 µl inhibitor (either Compound 5c or Compound 9e) in DMSO was added to 6 ml corn oil, and the rats were gavaged with 0.5 ml corn oil containing DMSO or containing DMSO and inhibitor.

Figure 2:
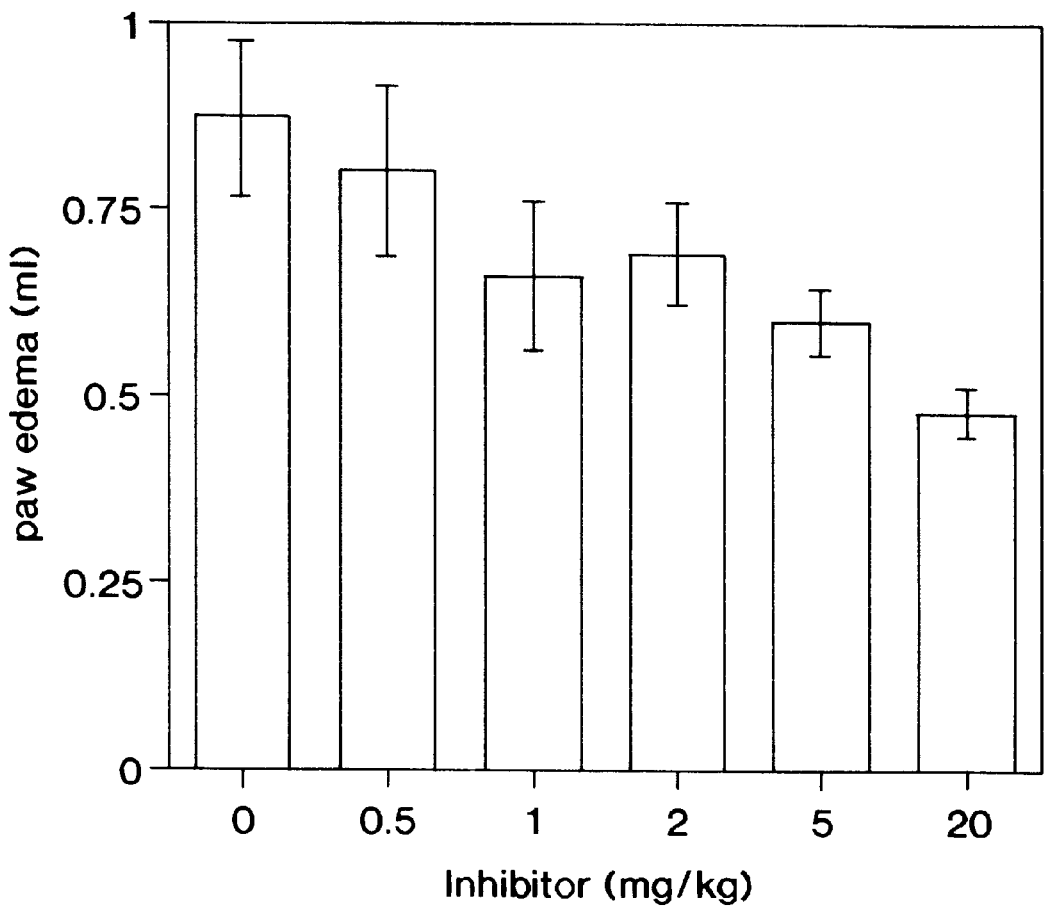
FIG. 2 is a graph illustrating inhibition of edema in the rat footpad by Compound 5c.
Figure 3:
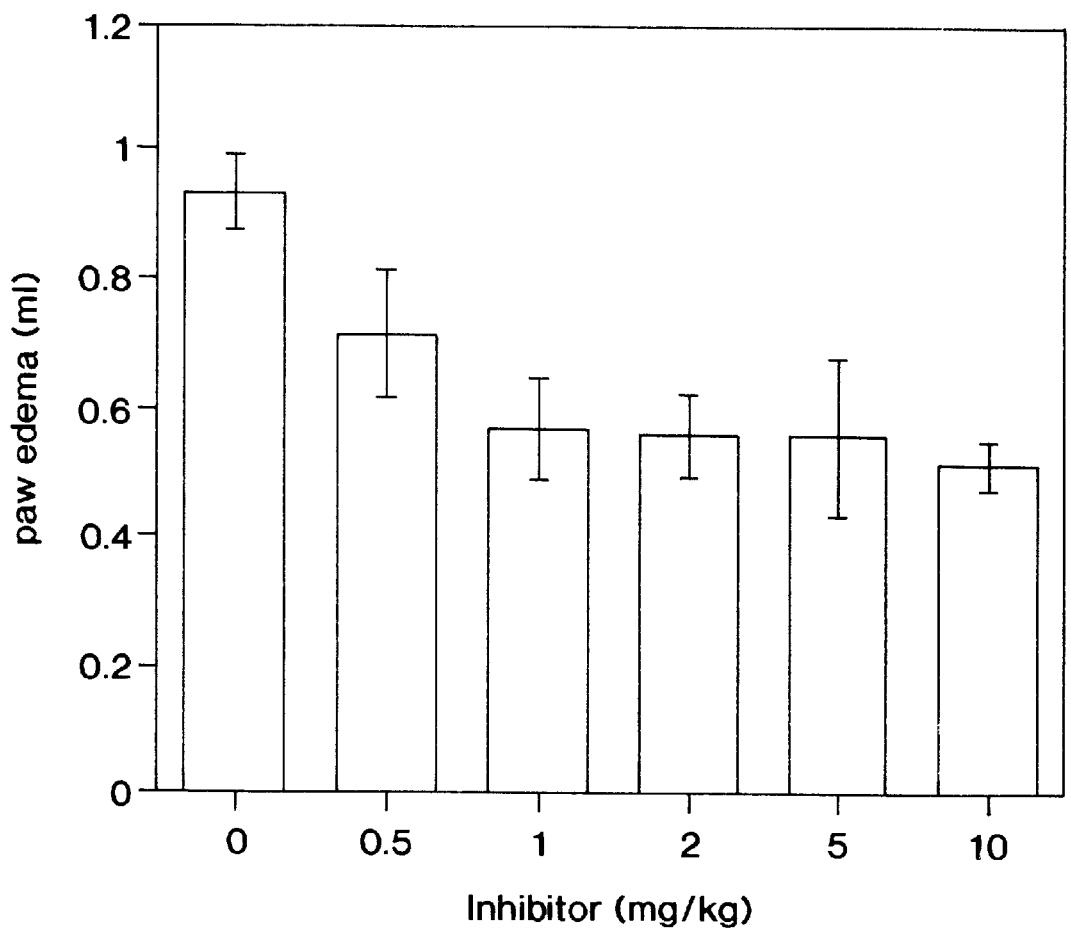
FIG. 3 is a graph illustrating inhibition of edema in the rat footpad by Compound 9e.

The ipsilateral footpad volume was measured with a water displacement plethysmometer (Ugo Basile, Italy, distributed by Stoelting Co., Wood Dale, Ill.) at 3 hour post-injection and compared to the initial pre-injection paw volume. Inhibitor concentrations were varied as shown in FIG. 2 (Compound 5c) and FIG. 3 (Compound 9e), with n=6 animals per group in duplicate experiments.

Example IV

Inhibition of COX-2 Activity in Intact Activated RAW 264.7 Cells by Indolealkanol Ester Compound 5c, Indolealkanol Ester Compound 5e, and Indolealkanol Amide Compound 9e The ability of these compounds to inhibit COX-2 in intact cells was assayed in activated RAW264.7 macrophages in which COX-2 activity was induced by pathologic stimuli. The macrophages were treated with lipopolysaccharide (500 mg/mL) and γ-interferon (10 U/mL) for 7.5 hours to induce COX-2 and then treated with several concentrations of each of inventive Compounds 5c, 5e, and 9e.

More specifically, low passage number murine RAW264.7 cells were grown in DMEM containing 10% heat-inactivated FBS. Cells (6.2×10$^6$ cells/T25 flask) were activated with 500 ng/mL LPS and 10 units/mL IFN-γ in serum-free DMEM for 7 hours. Vehicle (DMSO) or inhibitor (inventive Compound 5c, 5e, or 9e) in DMSO (0–1 µM) was added for 30 minutes at 37° C. Inhibition of exogenous arachidonic acid metabolism or inhibition of $PGD_2$ synthesis was determined by incubating the cells with 20 µM [1-$^{14}$C]-arachidonic acid, respectively, for 15 minutes at 25° C. Aliquots (200 µL) were removed into termination solution and total products were quantitatively determined by the TLC assay as described earlier.

The results are summarized in the graph of FIG. 1. Thus, in addition to inhibition of purified COX-2, these compounds are potent inhibitors of COX-2 activity in cultured inflammatory cells.

Example V representative Compounds of Formulae I and II

Table 3 sets forth representative amide compounds of Formula II having representative R, $R_1$, $R_2$, $R_3$, and $R_4$ group substituents, and Table 4 sets forth representative ester compounds of Formula I having representative R, $R_1$, $R_2$, $R_3$, and $R_4$ group substituents, in accordance with the present invention.

TABLE 3
N-(Substituted)-5-substituted-2-alkylindole-3-ethylamides
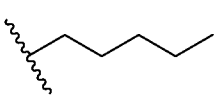
| Compd | R₁ | R₃ | R₂ | R₄ | R |
|---|---|---|---|---|---|
| 9a | OCH₃ | 4-Cl-C₆H₄-C(O)- | CH₃ | H | n-pentyl |
| 9b | OCH₃ | 4-Cl-C₆H₄-C(O)- | CH₃ | H | 4-CH₃-C₆H₄- |
| 9c | OCH₃ | 4-Cl-C₆H₄-C(O)- | CH₃ | H | 4-OCH₃-C₆H₄- |
| 9d | OCH₃ | 4-Cl-C₆H₄-C(O)- | CH₃ | H | 2-OCH₃-C₆H₄- |
| 9e | OCH₃ | 4-Cl-C₆H₄-C(O)- | CH₃ | H | 4-Cl-C₆H₄- |
| 9f | OCH₃ | 4-Cl-C₆H₄-C(O)- | CH₃ | H | 4-Br-C₆H₄- |
| 9g | OCH₃ | 4-Cl-C₆H₄-C(O)- | CH₃ | H | 4-I-C₆H₄- |

TABLE 3-continued

N-(Substituted)-5-substituted-2-alkylindole-3-ethylamides

[Structure: indole with R1 at 5-position, R2 at 2-position, R3 on N1, and a 3-(CH2CH2-N(R4)-C(=O)-R) side chain]

| Compd | R$_1$ | R$_3$ | R$_2$ | R$_4$ | R |
|---|---|---|---|---|---|
| 9h | OCH$_3$ | -CH$_2$-(4-Br-C$_6$H$_4$) | CH$_3$ | H | -(4-Cl-C$_6$H$_4$) |
| 9i | OCH$_3$ | -C(=O)-(4-Cl-C$_6$H$_4$) | CH$_3$ | H | -CH$_2$CH$_2$-C$_6$H$_5$ |
| 9j | OCH$_3$ | -CH$_2$-(4-Br-C$_6$H$_4$) | CH$_3$ | H | CH$_3$ |
| 9k | OCH$_3$ | -CH$_2$-(4-Br-C$_6$H$_4$) | H | H | CH$_3$ |
| 9l | OCH$_3$ | -C(=O)-(4-Cl-C$_6$H$_4$) | H | H | CH$_3$ |
| 9m | OCH$_3$ | -CH$_2$-(4-Br-C$_6$H$_4$) | CH$_3$ | H | CH$_2$CH$_2$ |
| 9n | Cl | -C(=O)-(4-Cl-C$_6$H$_4$) | CH$_3$ | H | CH$_3$ |
| 9o | Cl | -CH$_2$-(4-Br-C$_6$H$_4$) | CH$_3$ | H | CH$_3$ |

TABLE 3-continued

N-(Substituted)-5-substituted-2-alkylindole-3-ethylamides

| Compd | R₁ | R₃ | R₂ | R₄ | R |
|---|---|---|---|---|---|
| 9p | Cl | 4-chlorobenzoyl | CH₃ | CH₃ | CH₃ |
| 9q | Cl | 4-bromobenzyl | CH₃ | CH₃ | CH₃ |
| 9r | Cl | 4-bromobenzyl | CH₃ | H | 4-chlorophenyl |
| 9s | Cl | 4-chlorobenzoyl | CH₃ | H | 4-chlorophenyl |
| 9t | Cl | 4-chlorobenzoyl | CH₃ | CH₃ | 4-chlorophenyl |
| 9u | OCH₃ | 4-chlorobenzyl | CH₃ | H | 4-chlorophenyl |
| 9v | OCH₃ | 4-chlorobenzyl | CH₃ | H | 2-phenylethyl |

TABLE 3-continued
N-(Substituted)-5-substituted-2-alkylindole-3-ethylamides
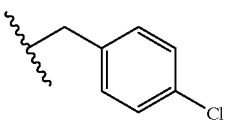
| Compd | R₁ | R₃ | R₂ | R₄ | R |
|---|---|---|---|---|---|
| 9w | OCH₃ | 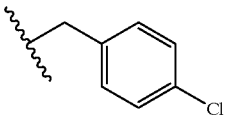 | CH₃ | H | CH₃ |
| 9x | OCH₃ | 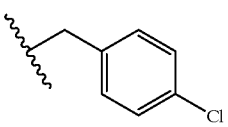 | CH₃ | CH₃ | CH₃ |
| 9y | OCH₃ | 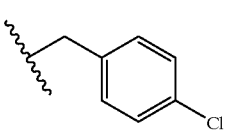 | CH₃ | H | CH₂CH₃ |
| 9z | OCH₃ | 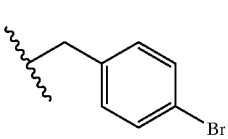 | CH₃ | CH₃ | CH₂CH₃ |
| 9aa | OCH₃ | 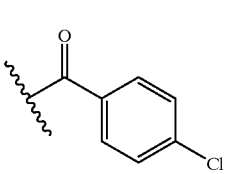 | CH₃ | H | CH₂COOCH₃ |
| 9bb | OCH₃ | 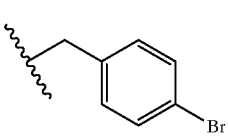 | CH₃ | H | CH₂COOCH₃ |
| 9cc | OCH₃ | 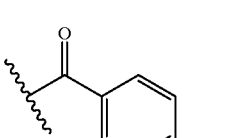 | CH₃ | H | CH₂COOH |
| 9dd | OCH₃ |  | CH₃ | H | CH₂COOH |

TABLE 3-continued

N-(Substituted)-5-substituted-2-alkylindole-3-ethylamides

| Compd | R₁ | R₃ | R₂ | R₄ | R |
|---|---|---|---|---|---|
| 9ee | OCH₃ | 4-Br-benzyl | CH₃ | CH₃ | CH₂COOH |
| 9ff | OCH₃ | 4-Br-benzyl | CH₃ | H | CH₂N(CH₃)₂ |
| 9gg | OCH₃ | 4-Cl-benzoyl | CH₃ | H | CH₂N(CH₃)₂ |
| 9hh | OCH₃ | 4-Cl-benzoyl | CH₃ | H | CH₂-(4-pyridyl) |
| 9ii | OCH₃ | 4-Br-benzyl | CH₃ | H | CH₂-(4-pyridyl) |
| 9jj | OCH₃ | 4-Cl-benzoyl | CH₃ | H | CH₂-(2-thiazolyl) |
| 9kk | OCH₃ | 4-Br-benzyl | CH₃ | H | CH₂-(2-thiazolyl) |
| 9ll | OCH₃ | 4-Br-benzyl | CH₃ | H | CH₂CH₂-phenyl |

TABLE 3-continued

N-(Substituted)-5-substituted-2-alkylindole-3-ethylamides

| Compd | R₁ | R₃ | R₂ | R₄ | R |
|---|---|---|---|---|---|
| 9mm | OCH₃ | 4-bromobenzyl | CH₃ | H | morpholinoethyl |
| 9nn | OCH₃ | 4-chlorobenzoyl | CH₃ | H | morpholinoethyl |
| 9oo | OCH₃ | 4-bromobenzyl | CH₃ | H | (CH₂)₂OH |
| 9pp | OCH₃ | 4-chlorobenzoyl | CH₃ | H | (CH₂)₂OH |
| 9qq | OCH₃ | 4-bromobenzyl | CH₃ | H | (5-methyl-1,3,4-thiadiazol-2-yl)methyl |
| 9rr | OCH₃ | 4-chlorobenzoyl | CH₃ | H | (5-methyl-1,3,4-thiadiazol-2-yl)methyl |
| 9ss | OCH₃ | 4-bromobenzyl | CH₃ | H | (6-oxo-1,6-dihydropyridazin-3-yl)methyl |
| 9tt | OCH₃ | 4-bromobenzyl | CH₃ | H | (6-oxo-1,6-dihydropyridazin-3-yl)methyl |

TABLE 3-continued

N-(Substituted)-5-substituted-2-alkylindole-3-ethylamides

| Compd | R₁ | R₃ | R₂ | R₄ | R |
|---|---|---|---|---|---|
| 9uu | OCH₃ | -CH₂-C₆H₄-Br (4-) | CH₃ | H | 6-oxo-1,6-dihydropyridazin-3-yl-methyl |
| 9vv | OCH₃ | -C(O)-C₆H₄-Cl (4-) | CH₃ | H | 5-methyloxazol-2-yl |
| 9ww | OCH₃ | -CH₂-C₆H₄-Br (4-) | CH₃ | H | (4-trifluoromethyl-pyrazol-1-yl)methyl |
| 9xx | OCH₃ | -C(O)-C₆H₄-Cl (4-) | CH₃ | H | (4-trifluoromethyl-pyrazol-1-yl)methyl |
| 9yy | OCH₃ | -CH₂-C₆H₄-Br (4-) | CH₃ | H | (5-trifluoromethyl-isoxazol-3-yl)methyl |
| 9zz | OCH₃ | -C(O)-C₆H₄-Cl (4-) | CH₃ | H | (5-trifluoromethyl-isoxazol-3-yl)methyl |
| 9aaa | OCH₃ | -CH₂-(pyridin-3-yl) | CH₃ | H | CH₂COOCH₃ |
| 9bbb | OCH₃ | -CH₂-(5-bromothiazol-2-yl) | CH₃ | H | CH₂COOCH₃ |

TABLE 3-continued
N-(Substituted)-5-substituted-2-alkylindole-3-ethylamides
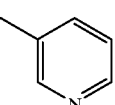
| Compd | R₁ | R₃ | R₂ | R₄ | R |
|---|---|---|---|---|---|
| 9ccc | OCH₃ | 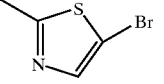 | CH₃ | H | CH₂COOH |
| 9ddd | OCH₃ | 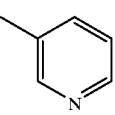 | CH₃ | H | CH₂COOH |
| 9eee | OCH₃ | 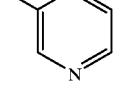 | CH₃ | CH₃ | CH₂COOH |
| 9fff | OCH₃ | 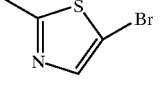 | CH₃ | H | CH₂N(CH₃)₂ |
| 9ggg | OCH₃ | 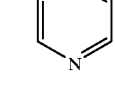 | CH₃ | H | CH₂N(CH₃)₂ |
| 9hhh | OCH₃ | 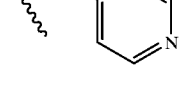 | CH₃ | H | 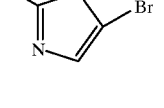 |
| 9iii | OCH₃ | 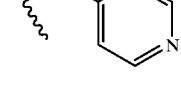 | CH₃ | H | 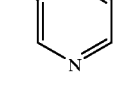 |
| 9jjj | OCH₃ | 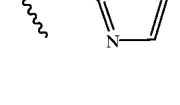 | CH₃ | H | 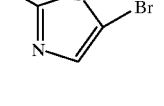 |
| 9kkk | OCH₃ | 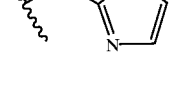 | CH₃ | H | 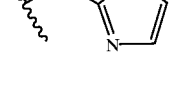 |

TABLE 3-continued
N-(Substituted)-5-substituted-2-alkylindole-3-ethylamides
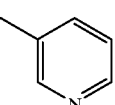
| Compd | R₁ | R₃ | R₂ | R₄ | R |
|---|---|---|---|---|---|
| 9lll | OCH₃ | 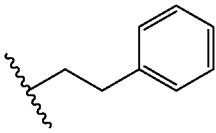 | CH₃ | H | 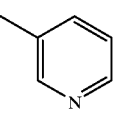 |
| 9mmm | OCH₃ | 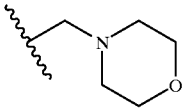 | CH₃ | H | 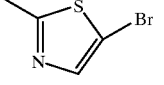 |
| 9nnn | OCH₃ | 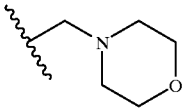 | CH₃ | H | 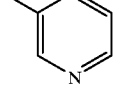 |
| 9ooo | Br | 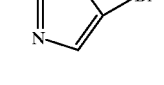 | CH₃ | H | CH₂COOCH₃ |
| 9ppp | Br | 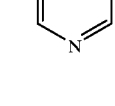 | CH₃ | H | CH₂COOCH₃ |
| 9qqq | Br | 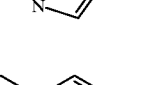 | CH₃ | H | CH₂COOH |
| 9rrr | Br | 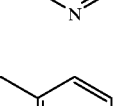 | CH₃ | H | CH₂COOH |
| 9sss | Br |  | CH₃ | CH₃ | CH₂COOH |
| 9ttt | Br |  | CH₃ | H | CH₂N(CH₃0)₂ |

TABLE 3-continued
N-(Substituted)-5-substituted-2-alkylindole-3-ethylamides
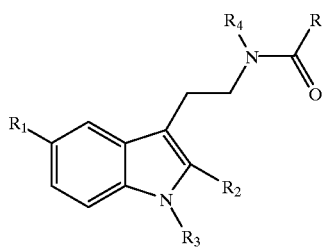
| Compd | R₁ | R₃ | R₂ | R₄ | R |
|---|---|---|---|---|---|
| 9uuu | Br | 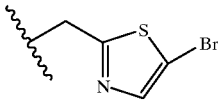 | CH₃ | H | CH₂N(CH₃)₂ |
| 9vvv | Br | 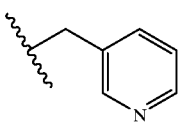 | CH₃ | H | 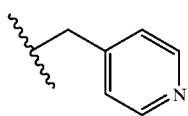 |
| 9www | Br | 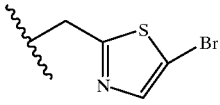 | CH₃ | H | 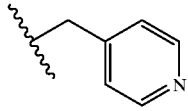 |
| 9xxx | Br | 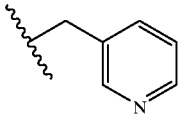 | CH₃ | H | 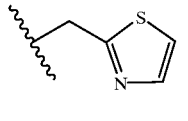 |
| 9yyy | Br | 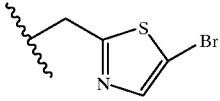 | CH₃ | H | 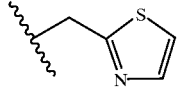 |
| 9zzz | Br | 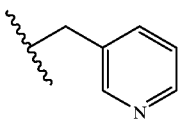 | CH₃ | H | 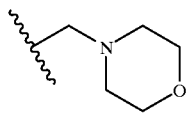 |

TABLE 4
N-(Substituted)-5-substituted-2-alkylindole-3-ethylesters
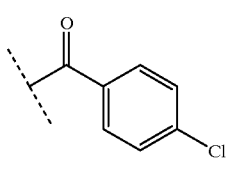
| Compound | R₁ | R₃ | R₂ | R |
|---|---|---|---|---|
| 5a | OCH₃ | 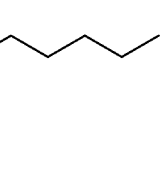 | CH₃ | 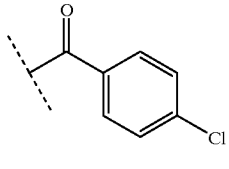 |
| 5b | OCH₃ | 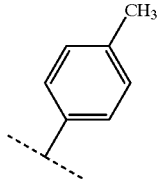 | CH₃ | 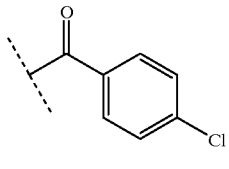 |
| 5c | OCH₃ | 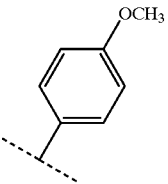 | CH₃ | 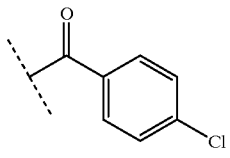 |
| 5d | OCH₃ | 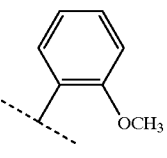 | CH₃ | 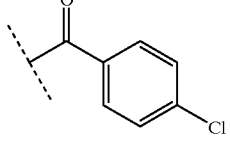 |
| 5e | OCH₃ | 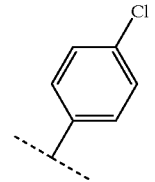 | CH₃ | 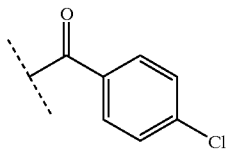 |
| 5f | OCH₃ | 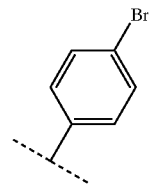 | CH₃ |  |

TABLE 4-continued

N-(Substituted)-5-substituted-2-alkylindole-3-ethylesters

[Structure: indole with R₁ at 5-position, R₂ at 2-position, R₃ on N, and a -CH₂CH₂-O-C(=O)-R group at 3-position]

| Compound | R₁ | R₃ | R₂ | R |
|---|---|---|---|---|
| 5g | OCH₃ | -C(=O)-C₆H₄-Cl (4-Cl benzoyl) | CH₃ | -C₆H₄-I (4-iodophenyl) |
| 5h | OCH₃ | -CH₂-C₆H₄-Br (4-bromobenzyl) | CH₃ | -C₆H₄-Cl (4-chlorophenyl) |
| 5i | OCH₃ | -C(=O)-C₆H₄-Cl (4-Cl benzoyl) | CH₃ | -CH₂CH₂-C₆H₅ (phenethyl-CH₂) |
| 5j | OCH₃ | -CH₂-C₆H₄-Br (4-bromobenzyl) | CH₃ | CH₃ |
| 5k | OCH₃ | -CH₂-C₆H₄-Br (4-bromobenzyl) | H | CH₃ |
| 5l | OCH₃ | -C(=O)-C₆H₄-Cl (4-Cl benzoyl) | H | CH₃ |
| 5m | OCH₃ | -CH₂-C₆H₄-Br (4-bromobenzyl) | CH₃ | CH₂CH₃ |

TABLE 4-continued

N-(Substituted)-5-substituted-2-alkylindole-3-ethylesters

| Compound | R₁ | R₃ | R₂ | R |
|----------|----|----|----|----|
| 5n | Cl | 4-chlorobenzoyl | CH₃ | CH₃ |
| 5o | Cl | 4-bromobenzyl | CH₃ | CH₃ |
| 5p | Cl | 4-chlorobenzoyl | CH₃ | CH₃ |
| 5q | Cl | 4-bromobenzyl | CH₃ | CH₃ |
| 5r | Cl | 4-bromobenzyl | CH₃ | 4-chlorophenyl |
| 5s | Cl | 3,4-dichlorobenzoyl | CH₃ | 4-chlorophenyl |
| 5t | Cl | 4-chlorobenzoyl | CH₃ | 4-chlorophenyl |

TABLE 4-continued
N-(Substituted)-5-substituted-2-alkylindole-3-ethylesters
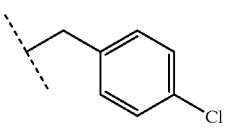
| Compound | R₁ | R₃ | R₂ | R |
|---|---|---|---|---|
| 5u | OCH₃ | 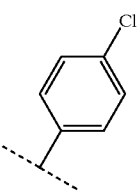 | CH₃ | 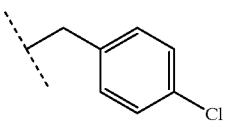 |
| 5v | OCH₃ | 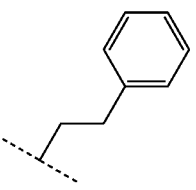 | CH₃ | 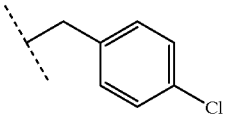 |
| 5w | OCH₃ | 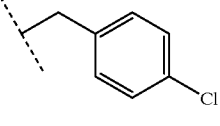 | CH₃ | CH₃ |
| 5x | OCH₃ | 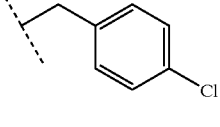 | CH₃ | CH₃ |
| 5y | OCH₃ | 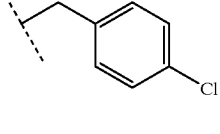 | CH₃ | CH₂CH₃ |
| 5z | OCH₃ | 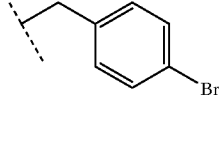 | CH₃ | CH₂CH₃ |
| 5aa | OCH₃ | (4-Br-benzyl) | CH₃ | CH₂COOCH₃ |

TABLE 4-continued

N-(Substituted)-5-substituted-2-alkylindole-3-ethylesters

| Compound | R₁ | R₃ | R₂ | R |
|---|---|---|---|---|
| 5bb | OCH₃ | 4-chlorobenzoyl | CH₃ | CH₂COOCH₃ |
| 5cc | OCH₃ | 4-bromobenzyl | CH₃ | CH₂COOH |
| 5dd | OCH₃ | 4-chlorobenzoyl | CH₃ | CH₂COOH |
| 5ee | OCH₃ | 4-bromobenzyl | CH₃ | CH₂COOH |
| 5ff | OCH₃ | 4-bromobenzyl | CH₃ | CH₂N(CH₃)₂ |
| 5gg | OCH₃ | 4-chlorobenzoyl | CH₃ | CH₂N(CH₃)₂ |
| 5hh | OCH₃ | 4-chlorobenzoyl | CH₃ | 4-pyridylmethyl |
| 5ii | OCH₃ | 4-bromobenzyl | CH₃ | 4-pyridylmethyl |

TABLE 4-continued

N-(Substituted)-5-substituted-2-alkylindole-3-ethylesters

| Compound | R₁ | R₃ | R₂ | R |
|---|---|---|---|---|
| 5jj | OCH₃ | 4-chlorobenzoyl | CH₃ | -CH₂-(2-thiazolyl) |
| 5kk | OCH₃ | 4-bromobenzyl | CH₃ | -CH₂-(2-thiazolyl) |
| 5ll | OCH₃ | 4-bromobenzyl | CH₃ | -CH(CH₂CH₂-phenyl) |
| 5mm | OCH₃ | 4-bromobenzyl | CH₃ | -CH₂-morpholinyl |
| 5nn | OCH₃ | 4-chlorobenzoyl | CH₃ | -CH₂-morpholinyl |
| 5oo | OCH₃ | 4-bromobenzyl | CH₃ | (CH₂)₂OH |
| 5pp | OCH₃ | 4-chlorobenzoyl | CH₃ | (CH₂)₂OH |

TABLE 4-continued

N-(Substituted)-5-substituted-2-alkylindole-3-ethylesters

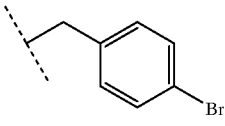

| Compound | R₁ | R₃ | R₂ | R |
|---|---|---|---|---|
| 5qq | OCH₃ | 4-Br-benzyl | CH₃ | 5-methyl-1,3,4-thiadiazol-2-yl |
| 5rr | OCH₃ | 4-Cl-benzoyl | CH₃ | 5-methyl-1,3,4-thiadiazol-2-yl |
| 5ss | OCH₃ | 4-Br-benzyl | CH₃ | 6-oxo-1,6-dihydropyridazin-3-yl |
| 5tt | OCH₃ | 4-Br-benzyl | CH₃ | 6-oxo-1,6-dihydropyridazin-3-yl |
| 5uu | OCH₃ | 4-Br-benzyl | CH₃ | 5-methyloxazol-2-yl |
| 5vv | OCH₃ | 4-Cl-benzoyl | CH₃ | 5-methyloxazol-2-yl |
| 5ww | OCH₃ | 4-Br-benzyl | CH₃ | 4-(trifluoromethyl)-1H-pyrazol-1-ylmethyl |
| 5xx | OCH₃ | 4-Cl-benzoyl | CH₃ | 4-(trifluoromethyl)-1H-pyrazol-1-ylmethyl |

TABLE 4-continued

N-(Substituted)-5-substituted-2-alkylindole-3-ethylesters

| Compound | R₁ | R₃ | R₂ | R |
|---|---|---|---|---|
| 5yy | OCH₃ | 4-bromobenzyl | CH₃ | (5-trifluoromethylisoxazol-3-yl)methyl |
| 5zz | OCH₃ | 4-chlorobenzoyl | CH₃ | (5-trifluoromethylisoxazol-3-yl)methyl |
| 5aaa | OCH₃ | (pyridin-3-yl)methyl | CH₃ | CH₂COOCH₃ |
| 5bbb | OCH₃ | (5-bromothiazol-2-yl)methyl | CH₃ | CH₂COOCH₃ |
| 5ccc | OCH₃ | (pyridin-3-yl)methyl | CH₃ | CH₂COOH |
| 5ddd | OCH₃ | (5-bromothiazol-2-yl)methyl | CH₃ | CH₂COOH |
| 5eee | OCH₃ | (pyridin-3-yl)methyl | CH₃ | CH₂COOH |
| 5fff | OCH₃ | (pyridin-3-yl)methyl | CH₃ | CH₂N(CH₃)₂ |
| 5ggg | OCH₃ | (5-bromothiazol-2-yl)methyl | CH₃ | CH₂N(CH₃)₂ |

TABLE 4-continued

N-(Substituted)-5-substituted-2-alkylindole-3-ethylesters

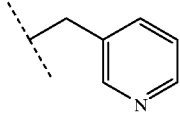

| Compound | R₁ | R₃ | R₂ | R |
|---|---|---|---|---|
| 5hhh | OCH₃ | 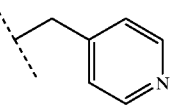 3-pyridyl-CH₂- | CH₃ | 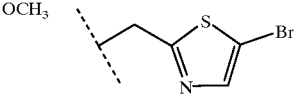 4-pyridyl-CH₂- |
| 5iii | OCH₃ | 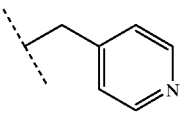 5-bromothiazol-2-yl-CH₂- | CH₃ | 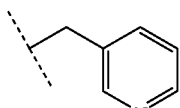 4-pyridyl-CH₂- |
| 5jjj | OCH₃ | 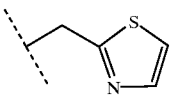 3-pyridyl-CH₂- | CH₃ | 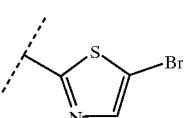 thiazol-2-yl-CH₂- |
| 5kkk | OCH₃ | 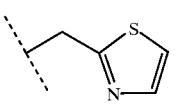 5-bromothiazol-2-yl-CH₂- | CH₃ | 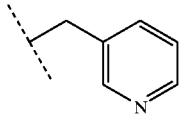 thiazol-2-yl-CH₂- |
| 5lll | OCH₃ | 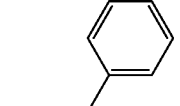 3-pyridyl-CH₂- | CH₃ | 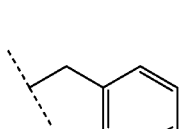 phenyl-CH₂CH₂- |
| 5mmm | OCH₃ | 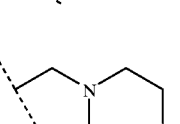 3-pyridyl-CH₂- | CH₃ | 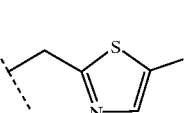 morpholinyl-CH₂- |
| 5nnn | OCH₃ | 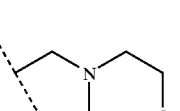 5-bromothiazol-2-yl-CH₂- | CH₃ | 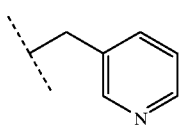 morpholinyl-CH₂- |
| 5ooo | Br | 3-pyridyl-CH₂- | CH₃ | CH₂COOCH₃ |

TABLE 4-continued

N-(Substituted)-5-substituted-2-alkylindole-3-ethylesters

| Compound | R₁ | R₃ | R₂ | R |
|---|---|---|---|---|
| 5ppp | Br | 2-(5-bromothiazolyl)methyl | CH₃ | CH₂COOCH₃ |
| 5qqq | Br | (3-pyridyl)methyl | CH₃ | CH₂COOH |
| 5rrr | Br | 2-(5-bromothiazolyl)methyl | CH₃ | CH₂COOH |
| 5sss | Br | (3-pyridyl)methyl | CH₃ | CH₂COOH |
| 5ttt | Br | (3-pyridyl)methyl | CH₃ | CH₂N(CH₃)₂ |
| 5uuu | Br | 2-(5-bromothiazolyl)methyl | CH₃ | CH₂N(CH₃)₂ |
| 5vvv | Br | (3-pyridyl)methyl | CH₃ | (4-pyridyl)methyl |
| 5www | Br | 2-(5-bromothiazolyl)methyl | CH₃ | (4-pyridyl)methyl |
| 5xxx | Br | (3-pyridyl)methyl | CH₃ | (2-thiazolyl)methyl |

TABLE 4-continued

N-(Substituted)-5-substituted-2-alkylindole-3-ethylesters

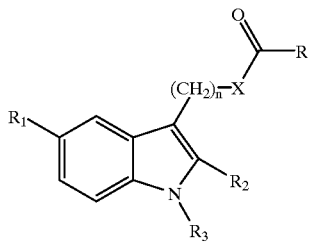

| Compound | $R_1$ | $R_3$ | $R_2$ | R |
|---|---|---|---|---|
| 5yyy | Br | (5-bromothiazol-2-yl)methyl | $CH_3$ | (thiazol-2-yl)methyl |
| 5zzz | Br | (pyridin-3-yl)methyl | $CH_3$ | morpholinomethyl |

It will be understood that various details of the invention may be changed without departing from the scope of the invention. Furthermore, the foregoing description is for the purpose of illustration only, and not for the purpose of limitation-the invention being defined by the claims.

What is claimed is:

1. A compound of the formula where:
R=$C_1$ to $C_6$ alkyl, $C_1$ to $C_6$ branched alkyl, $C_4$ to $C_8$ cycloalkyl, $C_1$ to $C_6$ hydroxyalkyl, branched $C_1$ to $C_6$ hydroxyalkyl, hydroxy substituted $C_4$ to $C_8$ aryl, primary, secondary or tertiary $C_1$ to $C_6$ alkylamino, primary, secondary or tertiary branched $C_1$ to $C_6$ alkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ aryl, $C_4$ to $C_8$ arylcarboxylic acid, $C_4$ to $C_8$ arylester, $C_4$ to $C_8$ aryl substituted $C_1$ to $C_6$ alkyl, $C_4$ to $C_8$ heterocyclic alkyl or aryl with O, N or S in the ring, alkyl-substituted or aryl-substituted $C_4$ to $C_8$ heterocyclic alkyl or aryl with O, N or S in the ring, or halo-substituted versions of the afore mentioned moieties defining R, where halo is chloro, bromo, fluoro or iodo, $R_1$=$C_1$ to $C_6$ alkyl, $C_1$ to $C_6$ branched alkyl, $C_4$ to $C_8$ cycloalkyl, $C_4$ to $C_8$ aryl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, or halo-substituted versions of the afore mentioned moieties defining $R_1$, or $R_1$ is halo, where halo is chloro, fluoro, bromo, or iodo, $R_2$=hydrogen, $C_1$ to $C_6$ alkyl or $C_1$ to $C_6$ branched alkyl, n=1, 2, 3, or 4, and when $R_3$=halobenzyl, then X=NH or N—$R_4$, where $R_4$=$C_1$ to $C_6$ alkyl or $C_1$ to $C_6$ branched alkyl, and when $R_3$=halobenzoyl, then X=O, and the compound possesses selectivity for inhibition of cyclooxygenase-2, where selectivity is at least 1015 for the ratio of $IC_{50}$ for cyclooxygenase-1 divided by $IC_{50}$ for cyclooxygenase-2.

2. The compound of claim 1, where:

R is selected from the group consisting of valeryl, methylphenyl, phenethyl, methoxy-phenyl, chlorophenyl, bromophenyl, and iodophenyl;

$R_1$ is methyl;

$R_2$ is methyl;

$R_3$ is selected from the group consisting of chlorobenzoyl, bromobenzoyl, and iodobenzoyl; and

X=O.

3. The compound of claim 2, where the compound is selected from the group consisting of N-(p-chlorobenzoyl)-5-methoxy-2-methylindole-3-ethyl-valerate, N-(p-chlorobenzoyl)-5-methoxy-2-methylindole-3-ethyl-(p-methyl)benzoate, N-(p-chlorobenzoyl)-5-methoxy-2-methylindole-3-ethyl-(p-methoxy) benzoate, N-(p-chlorobenzoyl)-5-methoxy-2-methylindole-3-ethyl-(o-methoxy) benzoate, N-(p-chlorobenzoyl)-5-methoxy-2-methylindole-3-ethyl-(p-chloro) benzoate, N-(p-chlorobenzoyl)-5-methoxy-2-methylindole-3-ethyl-(p-bromo) benzoate, N-(p-chlorobenzoyl)-5-methoxy-2-methylindole-3-ethyl-(p-iodo) benzoate, and N-(p-chlorobenzoyl)-5-methoxy-2-methylindole-3-ethyl-(2-phenyl)acetate.

4. The compound of claim 1, where:
R is selected from the group consisting of valeryl, methylphenyl, phenethyl, methoxy-phenyl, chlorophenyl, bromophenyl, and iodophenyl;
$R_1$ is methyl;
$R_2$ is methyl;
$R_3$ is selected from the group consisting of chlorobenzyl, bromobenzyl, and iodobenzyl; and
X is NH or N—$R_4$.

5. The compound of claim 4, where the compound is N-(p-bromobenzyl)-5-methoxy-2-methylindole-3-ethyl-(p-chloro)benzamide.

6. A method for analgesic, antiinflammatory, or antipyretic treatment in a warm blooded vertebrate animal, comprising administering to the animal a treatment-effective amount sufficient to create an analgesic, antiinflammatory, or antipyretic effect of a compound of the formula

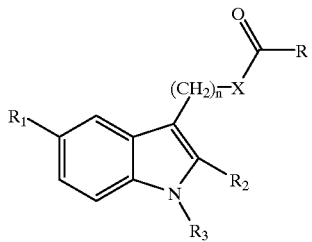

where:
R=$C_1$ to $C_6$ alkyl, $C_1$ to $C_6$ branched alkyl, $C_4$ to $C_8$ cycloalkyl, $C_1$ to $C_6$ hydroxyalkyl, branched $C_1$ to $C_6$ hydroxyalkyl, hydroxy substituted $C_4$ to $C_8$ aryl, primary, secondary or tertiary $C_1$ to $C_6$ alkylamino, primary, secondary or tertiary branched $C_1$ to $C_6$ alkylamino, primary, secondary or tertiary $C_4$ to $C_8$ arylamino, $C_1$ to $C_6$ alkylcarboxylic acid, branched $C_1$ to $C_6$ alkylcarboxylic acid, $C_1$ to $C_6$ alkylester, branched $C_1$ to $C_6$ alkylester, $C_4$ to $C_8$ aryl, $C_4$ to $C_8$ arylcarboxylic acid, $C_4$ to $C_8$ arylester, $C_4$ to $C_8$ aryl substituted $C_1$ to $C_6$ alkyl, $C_4$ to $C_8$ heterocyclic alkyl or aryl with O, N or S in the ring, alkyl-substituted or aryl-substituted $C_4$ to $C_8$ heterocyclic alkyl or aryl with O, N or S in the ring, or halo-substituted versions of the afore mentioned moieties defining R, where halo is chloro, bromo, fluoro or iodo, R=$C_1$ to $C_6$ alkyl, $C_1$ to $C_6$ branched alkyl, $C_4$ to $C_8$ cycloalkyl, $C_4$ to $C_8$ aryl, $C_4$ to $C_8$ aryl-substituted $C_1$ to $C_6$ alkyl, $C_1$ to $C_6$ alkoxy, $C_1$ to $C_6$ branched alkoxy, $C_4$ to $C_8$ aryloxy, or halo-substituted versions of the afore mentioned moieties defining $R_1$, or $R_1$ is halo, where halo is chloro, fluoro, bromo, or iodo, $R_2$=hydrogen, $C_1$ to $C_6$ alkyl or $C_1$ to $C_6$ branched alkyl, n=1, 2, 3, or 4, and
when $R_3$=halobenzyl, then X=NH or N—$R_4$, where $R_4$=$C_1$ to $C_6$ alkyl or $C_1$ to $C_6$ branched alkyl,
when $R_3$=halobenzoyl, then X=O,
and the compound possesses selectivity for inhibition of cyclooxygenase-2, where selectivity is at least 1015 for the ratio of $IC_{50}$ for cyclooxygenase-1 divided by $IC_{50}$ for cyclooxygenase-2.

7. The method of claim 6, wherein the treatment-effective amount sufficient to create and analgesic, antiinflammatory, or antipyretic effect ranges from about 0.5 milligram to about 7.0 milligrams per kilogram of body weight of the animal per day.

8. The method of claim 6, wherein the treatment effective amount sufficient to create an analgesic, antiinflammatory, or antipyretic effect ranges from about 1.5 milligrams to about 6.0 milligrams per kilogram of body weight of the animal per day.

9. The method of claim 6, wherein the treatment amount sufficient to create an analgesic, antiinflammatory, or antipyretic effect ranges from about 2.0 milligrams to about 5.0 milligrams per kilogram of body weight of the animal per day.

10. The method of claim 6, wherein the compound is selected from the group consisting of N-(p-chlorobenzoyl)-5-methoxy-2-methylindole-3-ethyl-valerate, N-(p-chlorobenzoyl)-5-methoxy-2-methylindole-3-ethyl-(p-methyl)benzoate, N-(p-chlorobenzoyl)-5-methoxy-2-methyl indole-3-ethyl-(p-methoxy) benzoate, N-(p-chlorobenzoyl)-5-methoxy-2-methylindole-3-ethyl-(o-methoxy) benzoate, N-(p-chlorobenzoyl)-5-methoxy-2-methylindole-3-ethyl-(p-chloro) benzoate, N-(p-chlorobenzoyl)-5-methoxy-2-methylindole-3-ethyl-(p-bromo) benzoate, N-(p-chlorobenzoyl)-5-methoxy-2-methylindole-3-ethyl-(p-iodo) benzoate, N-(p-bromobenzoyl)-5-methoxy-2-methylindole-3-ethyl-(p-chloro) benzoate, N-(p-chlorobenzoyl)-5-methoxy-2-methylindole-3-ethyl-(2-phenyl) acetate; N-(p-chlorobenzoyl)-5-methoxy-2-methyl indole-3-ethyl-valeramide, N-(p-chlorobenzoyl)-5-methoxy-2-methylindole-3-ethyl-(p-methyl)benzamide, N-(p-chlorobenzoyl)-5-methoxy-2-methylindole-3-ethyl-(p-methoxy)benzamide, N-(p-chlorobenzoyl)-5-methoxy-2-methylindole-3-ethyl-(o-methoxy)benzamide, N-(p-chlorobenzoyl)-5-methoxy-2-methylindole-3-ethyl-(p-chloro)benzamide, N-(p-chlorobenzoyl)-5-methoxy-2-methylindole-3-ethyl-(p-bromo)benzamide, N-(p-chlorobenzoyl)-5-methoxy-2-methylindole-3-ethyl-(p-iodo) benzamide, N-(p-bromobenzyl)-5-methoxy-2-methylindole-3-ethyl-(p-chloro)benzamide, and N-(p-chlorobenzoyl)-5-methoxy-2-methylindole-3-ethyl-(2-phenyl)ethylamide, and combinations thereof.

* * * * *

UNITED STATES PATENT AND TRADEMARK OFFICE
CERTIFICATE OF CORRECTION

PATENT NO. : 6,306,890 B1
DATED : October 23, 2001
INVENTOR(S) : Amit S. Kalgutkar et al.

It is certified that error appears in the above-identified patent and that said Letters Patent is hereby corrected as shown below:

Column 1,
Line 6, please insert the following:
-- GOVERNMENT INTEREST
This invention was made in part with government support under grant number CA47479 awarded by the National Institutes of Health. The United States government has certain rights in the invention. --.

Signed and Sealed this

Twentieth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,306,890 B1
DATED : October 23, 2001
INVENTOR(S) : Amit S. Kalgutkar et al.

It is certified that error appears in the above-identified patent and that said Letters Patent is hereby corrected as shown below:

Column 75,
Line 47, replace "R" with -- R1 --.

Signed and Sealed this

Seventh Day of February, 2006

JON W. DUDAS
*Director of the United States Patent and Trademark Office*